(12) United States Patent
Quinn et al.

(10) Patent No.: US 8,052,715 B2
(45) Date of Patent: Nov. 8, 2011

(54) METHOD AND APPARATUS FOR RECAPTURING AN IMPLANT FROM THE LEFT ATRIAL APPENDAGE

(75) Inventors: Chris Quinn, Minneapolis, MN (US); Jin Shimada, Grantsburg, WI (US); Kevin Anderson, Brooklyn Center, MN (US)

(73) Assignee: Atritech, Inc., Plymouth, MN (US)

( * ) Notice: Subject to any disclaimer, the term of this patent is extended or adjusted under 35 U.S.C. 154(b) by 621 days.

(21) Appl. No.: 11/607,266

(22) Filed: Dec. 1, 2006

(65) Prior Publication Data

US 2007/0129753 A1 Jun. 7, 2007

Related U.S. Application Data

(60) Provisional application No. 60/741,128, filed on Dec. 1, 2005.

(51) Int. Cl.
*A61M 29/00* (2006.01)
(52) U.S. Cl. ...................................... 606/200
(58) Field of Classification Search .................. 606/108, 606/110–114, 127, 128, 191, 192, 194, 198, 606/200, 205–208; 623/1.11, 1.12
See application file for complete search history.

(56) References Cited

U.S. PATENT DOCUMENTS

| | | |
|---|---|---|
| 4,611,594 A | 9/1986 | Grayhack et al. |
| 5,098,440 A | 3/1992 | Hillstead |
| 5,108,413 A | 4/1992 | Moyers |
| 5,211,658 A | 5/1993 | Clouse |
| 5,464,408 A | 11/1995 | Duc |
| 5,514,236 A | 5/1996 | Avellanet et al. |
| 5,634,942 A | 6/1997 | Chevillon et al. |
| 5,643,282 A | 7/1997 | Kieturakis |
| 5,690,611 A | 11/1997 | Swartz et al. |
| 5,709,704 A | 1/1998 | Nott et al. |
| 5,715,818 A | 2/1998 | Swartz et al. |
| 5,733,302 A | 3/1998 | Myler et al. |
| 5,772,678 A | 6/1998 | Thomason et al. |
| 5,807,261 A | 9/1998 | Benaron et al. |
| 5,814,029 A | 9/1998 | Hassett |
| 5,848,969 A | 12/1998 | Panescu et al. |
| 5,993,483 A | 11/1999 | Gianotti |
| 6,090,084 A | 7/2000 | Hassett et al. |
| 6,152,144 A | 11/2000 | Lesh et al. |
| 6,156,018 A | 12/2000 | Hassett |

(Continued)

FOREIGN PATENT DOCUMENTS

DE 3737121 A1 * 5/1989

(Continued)

*Primary Examiner* — Gary Jackson
*Assistant Examiner* — Lindsey Bachman
(74) *Attorney, Agent, or Firm* — Seager, Tufte & Wickhem LLC

(57) ABSTRACT

A system and method for retrieving an implantable device includes a delivery catheter, a recapture section, and a sheath. The delivery catheter has a proximal end and a distal end. The recapture section is axially extendable from the distal end of the delivery catheter. The sheath has a proximal end and a distal end and a lumen sized to receive the delivery catheter. A portion of the lumen of the sheath is actuatable from an enlarged inside diameter to a reduced inside diameter to apply an inwardly directed force to the recapture section. The delivery catheter can be actuated with respect to the sheath to extend or retract the recapture section with respect to the delivery catheter.

7 Claims, 21 Drawing Sheets

U.S. PATENT DOCUMENTS

| | | | |
|---|---|---|---|
| 6,156,055 A * | 12/2000 | Ravenscroft | 606/206 |
| 6,214,029 B1 | 4/2001 | Thill et al. | |
| 6,285,898 B1 | 9/2001 | Ben-Haim | |
| 6,371,971 B1 | 4/2002 | Tsugita et al. | |
| 7,044,134 B2 | 8/2002 | Khairkhahan et al. | |
| 6,447,530 B1 | 9/2002 | Ostrovsky et al. | |
| 6,514,280 B1 | 2/2003 | Gilson | |
| 6,551,303 B1 | 4/2003 | Van Tassel et al. | |
| 6,650,923 B1 | 11/2003 | Lesh et al. | |
| 6,837,901 B2 * | 1/2005 | Rabkin et al. | 623/1.11 |
| 7,056,294 B2 | 6/2006 | Khairkhahan et al. | |
| 7,128,073 B1 | 10/2006 | van der Burg et al. | |
| 2002/0035374 A1 * | 3/2002 | Borillo et al. | 606/194 |
| 2003/0144657 A1 | 7/2003 | Bowe et al. | |
| 2005/0038470 A1 * | 2/2005 | van der Burg et al. | 606/213 |
| 2005/0177182 A1 | 8/2005 | van der Burg et al. | |

FOREIGN PATENT DOCUMENTS

| | | |
|---|---|---|
| WO | WO 00/10452 | 3/2000 |

\* cited by examiner

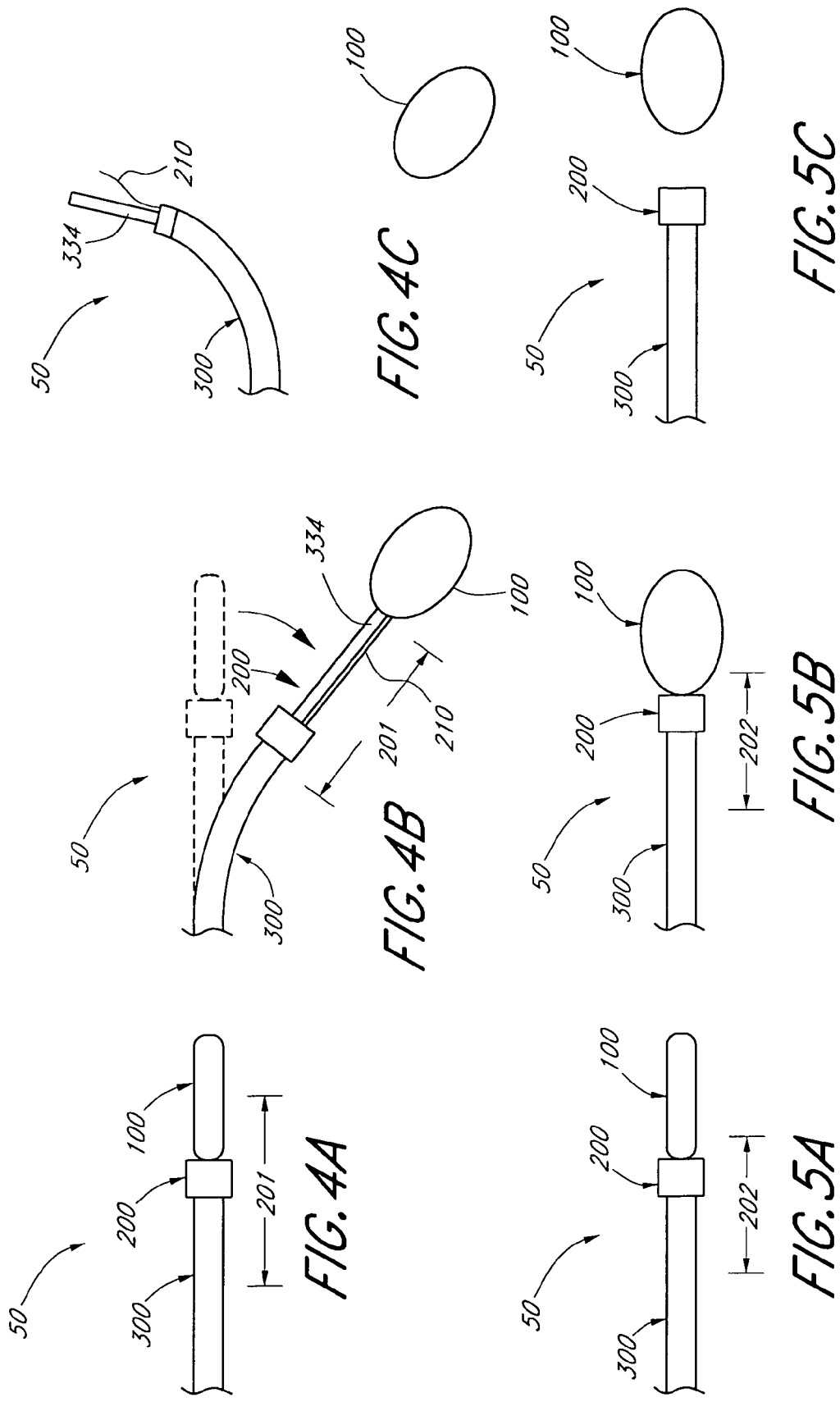

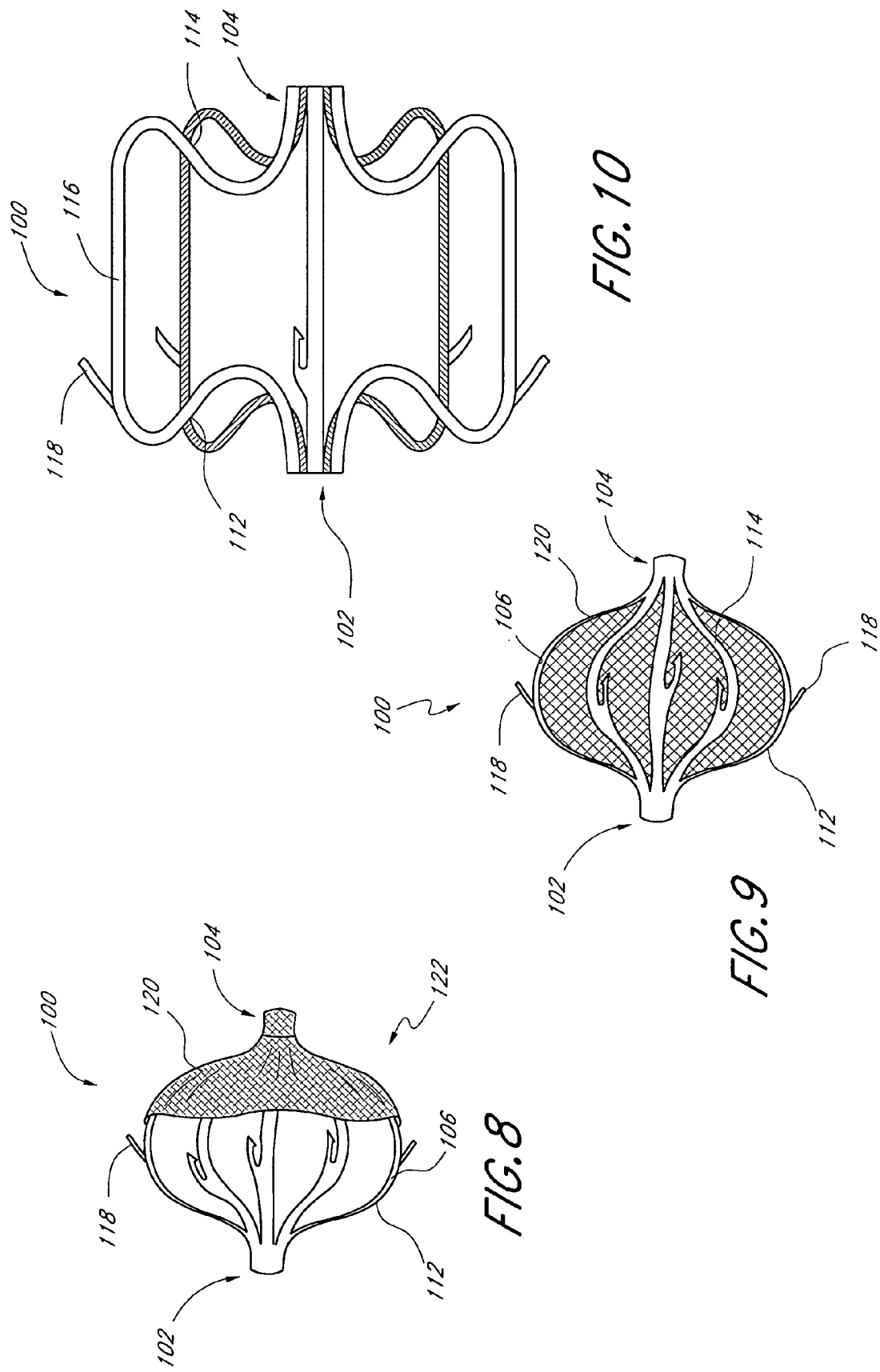

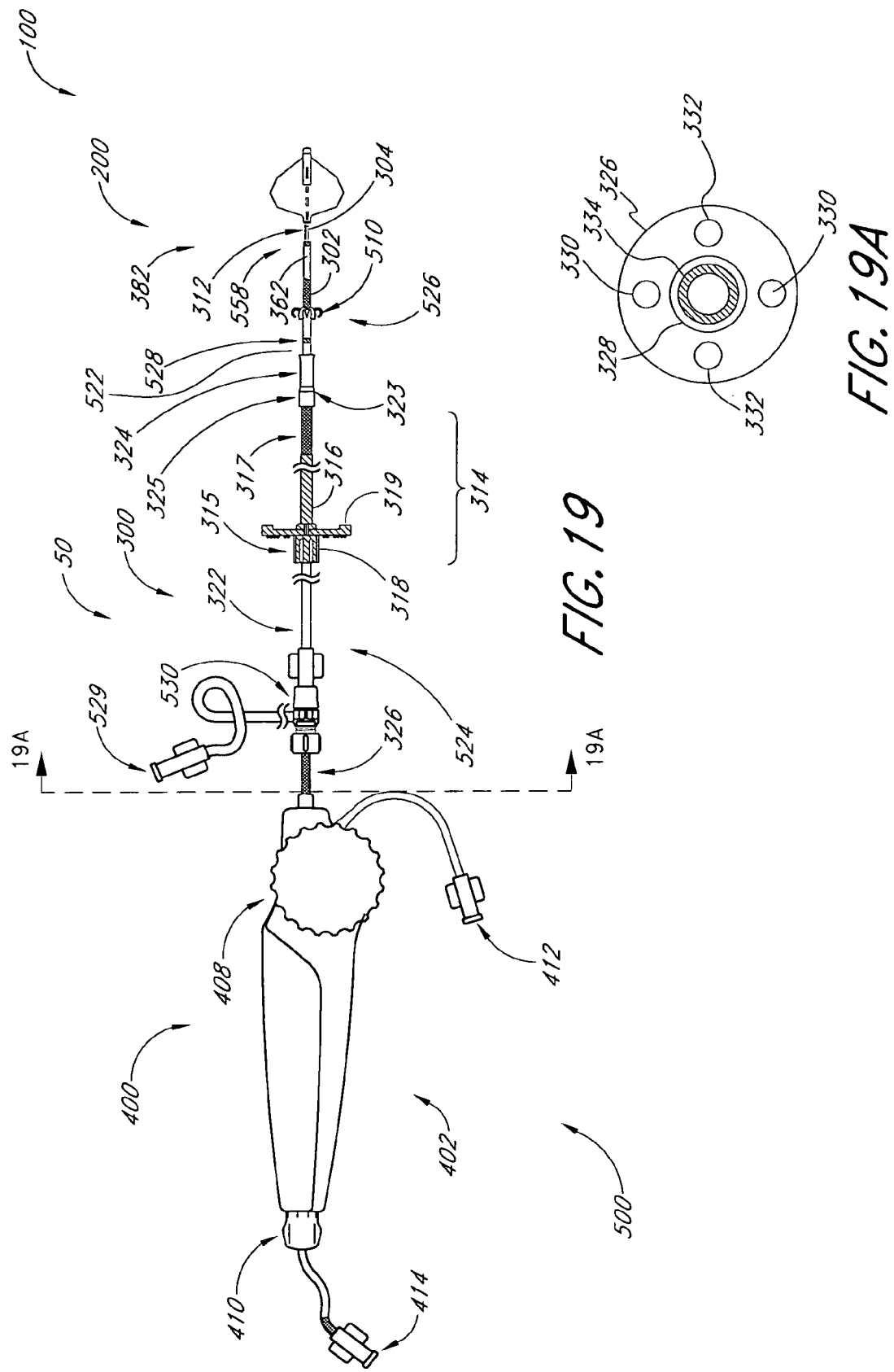

METHOD AND APPARATUS FOR RECAPTURING AN IMPLANT FROM THE LEFT ATRIAL APPENDAGE

CROSS-REFERENCE TO RELATED U.S. APPLICATIONS

This application claims the benefit of priority from U.S. Provisional No. 60/741,128, filed Dec. 1, 2005, which is incorporated by reference, herein.

BACKGROUND

Embolic stroke is the nation's third leading killer for adults, and is a major cause of disability. There are over 700,000 strokes per year in the United States alone. Of these, roughly 100,000 are hemorrhagic, and 600,000 are ischemic (either due to vessel narrowing or to embolism). The most common cause of embolic stroke emanating from the heart is thrombus formation due to atrial fibrillation. Approximately 80,000 strokes per year are attributable to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in part, to the fear of a stroke, and the pharmaceutical regimen necessary to reduce that risk.

For patients who develop atrial thrombus from atrial fibrillation, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with atrial fibrillation. As a result, thrombus formation is predisposed to form in the stagnant blood within the LAA.

Blackshear and Odell have reported that of the 1288 patients with non-rheumatic atrial fibrillation involved in their study, 221 (17%) had thrombus detected in the left atrium of the heart. Blackshear J L, Odell J A., Appendage Obliteration to Reduce Stroke in Cardiac Surgical Patients With Atrial Fibrillation. Ann Thorac. Surg., 1996.61(2):755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thorascopic surgical procedure often outweigh the potential benefits. See Blackshear and Odell, above. See also Lindsay B D., Obliteration of the Left Atrial Appendage: A Concept Worth Testing, Ann Thorac. Surg., 1996.61(2):515.

During surgical procedures, such as mitral valve repair, thrombus in the left atrial appendage may leave the LAA and enter the blood stream of a patient. The thrombus in the blood stream of the patient can cause embolic stroke. There are known techniques for closing off the LAA so that thrombus cannot enter the patient's blood stream. For example, surgeons have used staples or sutures to close the orifice of the LAA, such that the closed off LAA surrounds the thrombus. Unfortunately, using staples or sutures to close off the LAA may not completely close the orifice of the LAA. Thus, thrombus may leave the LAA and enter the patient's blood stream, even though the LAA is closed with staples or sutures. Additionally, closing the orifice of the LAA by using staples or sutures may result in discontinuities, such as folds or creases, in the endocardial surface facing the left atrium. Unfortunately, blood clots may form in these discontinuities and can enter the patient's blood stream, thereby causing health problems. Moreover, it is difficult to place sutures at the orifice of the LAA and may result in a residual appendage. For example, an epicardial approach to ligate sutures can result in a residual appendage. Similarly, thrombus may form in the residual appendage and enter the patient's blood stream causing health problems.

Despite the various efforts in the prior art, there remains a need for a minimally invasive method and associated devices for reducing the risk of thrombus formation in the left atrial appendage. Various implantable devices and methods of delivery and retrieval of these devices have been previously described. Some systems for deploying, releasing, repositioning, or recapturing an implant to or from the left atrial appendage of the heart are known to those of skill in the art. For example, U.S. application Ser. No. 10/642,384, filed Aug. 15, 2003, published as U.S. Publication No. 2005/0038470; U.S. application Ser. No. 11/607,638, filed Dec. 1, 2006, titled "METHOD AND APPARATUS FOR RETRIEVING AN EMBOLIZED IMPLANT"; U.S. application Ser. No. 11/607,253, filed Dec. 1, 2006, titled "METHOD AND APPARATUS FOR DELIVERING AN IMPLANT WITHOUT BIAS TO A LEFT ATRIAL APPENDAGE"; and U.S. application Ser. No. 11/607,769, filed Dec. 1, 2006, titled "METHOD FOR ACCESSING THE LEFT ATRIAL APPENDAGE WITH A BALLOON-TIPPED TRANSEPTAL SHEATH," are all incorporated by reference herein and describe several such systems. Some of the embodiments of some systems described in the references include a separate sheath for recapture of the implant into the delivery system once extra thickness and stiffness to the delivery system. When reducing delivery system thickness and increasing flexibility is desired, it would be advantageous to have a delivery system for providing an implant to the left atrial appendage, where an additional sheath is not used to recapture the implant.

SUMMARY OF THE INVENTION

There is provided in accordance with one embodiment of the present invention a system and method for retrieving an implantable device which includes a delivery catheter, a recapture section, and a sheath. In one embodiment the implant is configured for containing emboli with a left atrial appendage of a heart of a patient. The delivery catheter has a proximal end and a distal end. The recapture section is axially extendable from the distal end of the delivery catheter. The sheath has a proximal end and a distal end and a lumen sized to receive the delivery catheter. A portion of the lumen of the sheath is actuatable from an enlarged inside diameter to a reduced inside diameter to apply an inwardly directed force to the recapture section. The delivery catheter can be actuated with respect to the sheath to extend or retract the recapture section with respect to the delivery catheter.

In one embodiment a system for retrieving an implantable device is provided including a delivery catheter, a recapture section and a sheath. The delivery catheter has a proximal end and a distal end. The recapture section is axially extendable from the distal end of the delivery catheter. The sheath has a proximal end and a distal end and a lumen sized to receive the delivery catheter. A portion of the lumen of the sheath is actuatable from an enlarged inside diameter to a reduced inside diameter in order to apply an inwardly directed force to the recapture section.

In another embodiment a method provides for the retrieval of an implantable device. The method includes providing a sheath, providing a delivery catheter releasably coupled to an implantable device and to a recapture section, enlarging a portion of the sheath to engage the recapture section, advancing the sheath to move the recapture section toward an implantable device, releasing the sheath from engagement with the recapture section, and moving the delivery catheter proximally to move the implantable device into a lumen of the sheath. The sheath has a sheath proximal end and a sheath distal end and a lumen extending therethrough. The delivery catheter is releasably coupled to the implantable device. The delivery catheter has a catheter proximal end and a catheter distal end. The catheter extends through the lumen of the sheath. The recapture section is axially extendable from a distal portion of the delivery catheter. A portion of the sheath is enlarged within the lumen to engage the recapture section. The sheath is distally advanced while engaged with the recapture section to distally extend the recapture section relative to the distal end of the delivery catheter and to at least partially cover the implantable device. The sheath is released from engagement with the recapture section. The delivery catheter is moved proximally relative to the sheath to move the implantable device at least partially covered by the recapture section into the lumen of the sheath.

In another embodiment, a catheter for retrieving an implantable device is provided. The catheter includes an elongate tubular body, a tubular mesh and a recapture section. The elongate tubular body has a proximal end, a distal end and a distal portion adjacent the distal end. The tubular mesh is connected to the distal portion of the tubular body and is capable of stretching longitudinally. The recapture section is connected to the tubular mesh. The recapture section has a reduced configuration and an enlarged configuration capable of receiving at least a portion of the implantable device.

BRIEF DESCRIPTION OF THE DRAWINGS

FIG. 4A is a side elevational view of the distal end of the implant delivery system shown in FIG. 3A with a radially-reduced implant;

FIG. 4B is a side elevational view of the distal end of the implant delivery system shown in FIG. 4A with a radially-expanded implant;

FIG. 4C is a side elevational view of the distal end of an implant delivery system shown in FIG. 4B with a released radially-expanded implant;

FIG. 5A is a side elevational view of the distal end of the implant delivery system shown in FIG. 3B with a radially-reduced implant;

FIG. 5B is a side elevational view of the distal end of the implant delivery system shown in FIG. 5A with a radially-expanded implant;

FIG. 5C is a side elevational view of the distal end of an implant delivery system shown in FIG. 5B with a released radially-expanded implant;

FIGS. 8 and 9 are side elevational schematic representations of partial and complete barrier layers of the containment device of FIG. 7;

FIG. 10 is a side elevational schematic view of an alternate containment device in accordance with another embodiment of the present invention;

FIG. 19 is a schematic view of a delivery system in accordance with one embodiment of the present invention;

FIG. 19A is a cross-sectional view of an implant delivery system as shown in FIG. 19, taken along line 19A-19A;

DETAILED DESCRIPTION OF CERTAIN PREFERRED EMBODIMENTS

Figure 1:
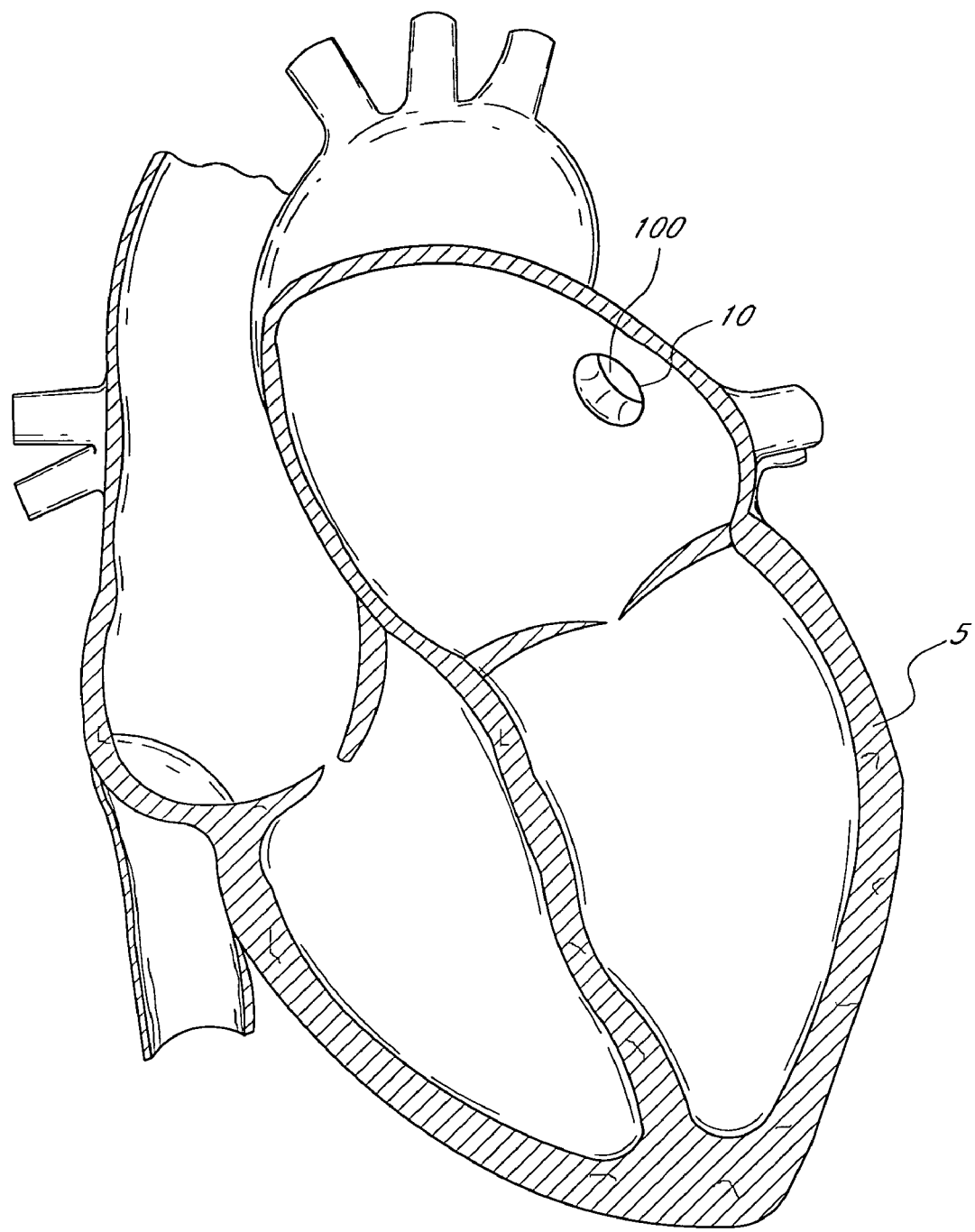
FIG. 1 is a view of a heart and its left atrial appendage.

FIG. 1 illustrates a sectional view of a heart 5 and its left atrial appendage (LAA) 10. An implant 100 is provided at least partially within the LAA 10. The terms "implant", "occlusion device" or "containment device" are broad terms intended to have their ordinary meaning. In addition, these terms are intended to refer to devices that are inserted into the body. Such devices may include a membrane, barrier and/or cover, or may omit these portions. Embodiments of the invention may also be used to treat other bodily openings, lumen and cavities, besides the LAA 10. For example, in some embodiments, the methods, devices and systems described herein are used to treat any heart opening or defect, such as a patent foramen ovale (PFO), an atrial septal defect (ASD), a ventricular septal defect (VSD), a patent ductus arteriosus (PDA), an aneurysm and/or an aortico-pulmonary window.

In various embodiments, an implant 100 can be delivered in a number of ways, e.g., using conventional transthoracic surgical, minimally invasive, or port access approaches. Delivery can be made or done in conjunction with surgical procedures as well. In one embodiment, the implant 100 is used in conjunction with various surgical heart procedures related to the heart (e.g., mitral valve repair) or surgical procedures in the region surrounding the heart. The delivery system can be used to locate and deploy the implant 100 in order to prevent the passage of embolic material from the LAA 10, such that thrombus remains contained in the LAA 10. Thrombus remains contained in the LAA 100 because the implant 100 inhibits thrombus within the LAA 10 from passing through the orifice of the LAA 10 and into the patient's blood stream. Additionally, the deployed implant 100 located in the LAA 10 can provide a smooth, non-thrombogenic surface facing the left atrium. In one embodiment, the smooth, non-thrombogenic surface facing the left atrium will not promote blood clots to form proximate to the LAA 10. Access to the heart may be provided by surgical procedures in order to deploy the implant 100 in the LAA 10. That is, the implant 100 can be deployed as an adjunct to surgical procedures. Various methods for accessing the LAA 10 and delivering an implant 100 to the LAA 10 are disclosed in U.S. application Ser. No. 11/003,696, filed Dec. 3, 2004, published as U.S. Publication No. 2005-0177182 A1, which is incorporated by reference herein.

A. Implant Delivery System

Figure 2:
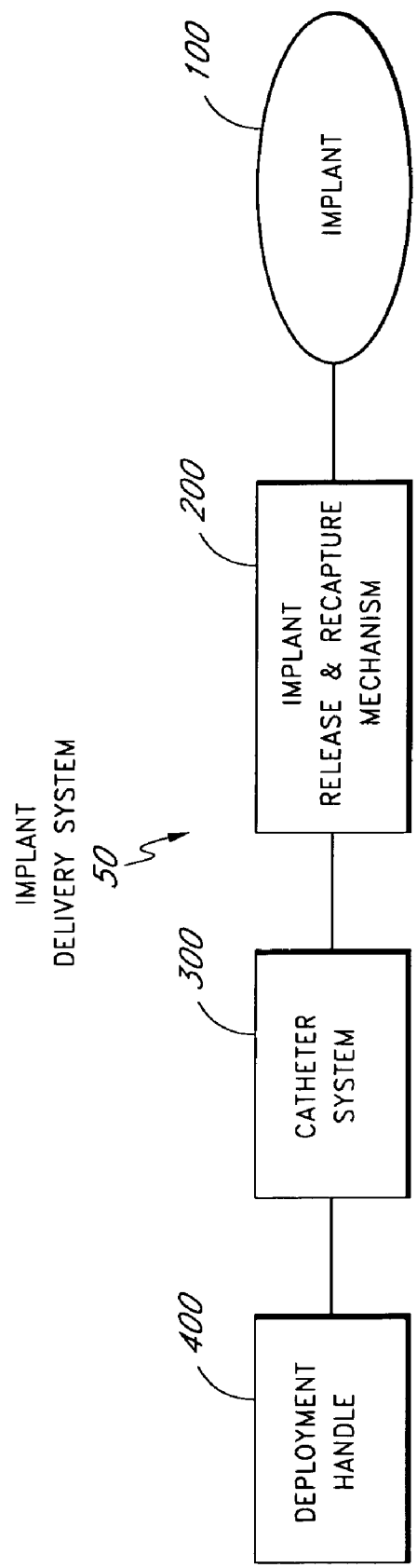
FIG. 2 is a block diagram representing an embodiment of a simplified implant delivery system in accordance with the present invention.

FIG. 2 illustrates a block diagram of an implant delivery system 50. The implant delivery system 50 includes an implant 100, an implant release and recapture mechanism 200, a catheter system 300 and a deployment handle 400. In some embodiments, the implant release and recapture mechanism 200 is the distal portion of the catheter system 300 and the deployment handle 400 is the proximal portion of the catheter system 300. The implant release and recapture mechanism 200 generally couples the implant 100 to the catheter system 300. The deployment handle 400 generally provides all the user controls and actuators of the implant delivery system 50.

Figure 2A:
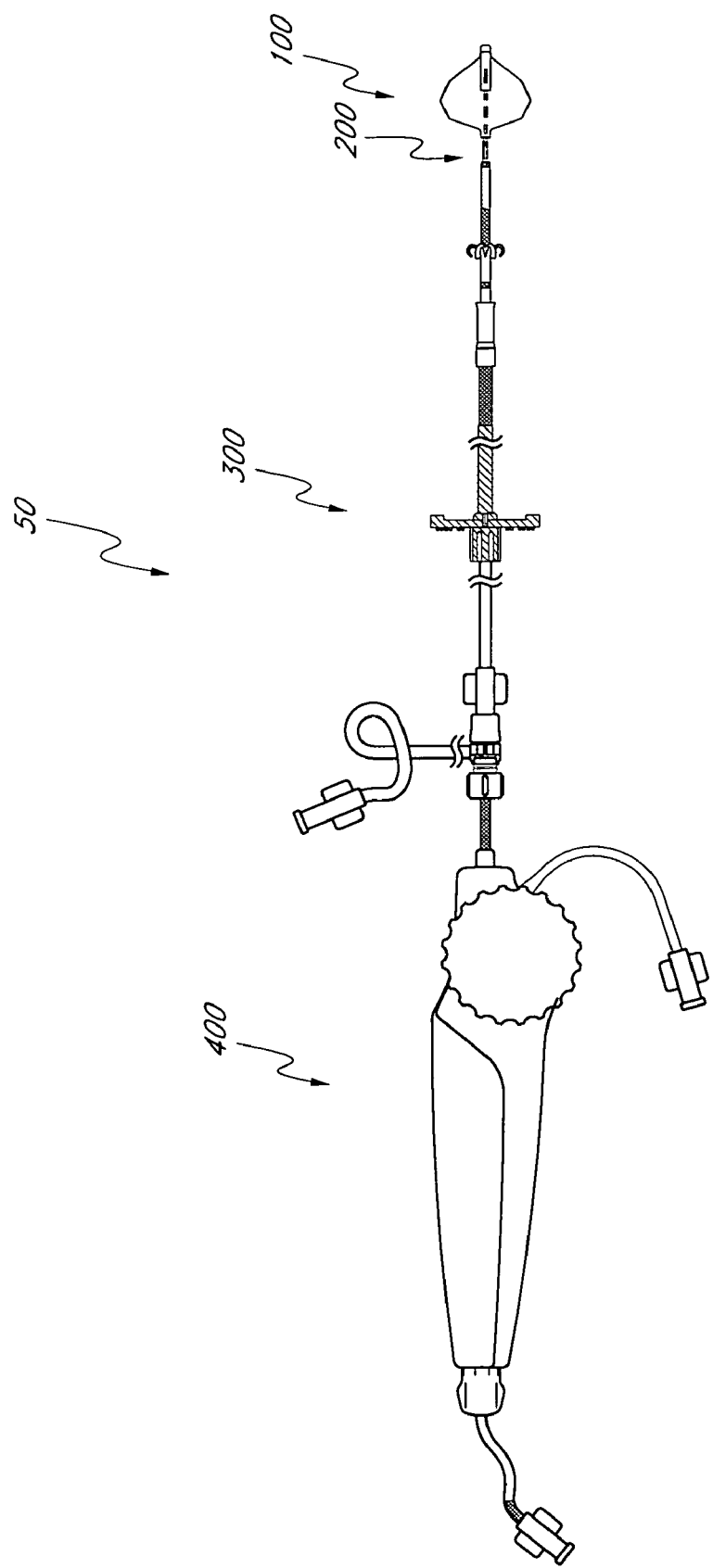
FIG. 2A is a schematic view of one embodiment of the delivery system of FIG. 2.

FIG. 2A illustrates one embodiment of the implant delivery system 50 of FIG. 2. The implant delivery system 50 includes an implant release and recapture mechanism 200 that is flexible and without bias. In this manner, when the implant 100 is released from the delivery system 50, the implant 100 maintains the position and orientation it had when coupled to the delivery system 50, and does not spring, jump, or move, as described above.

Figure 3A:
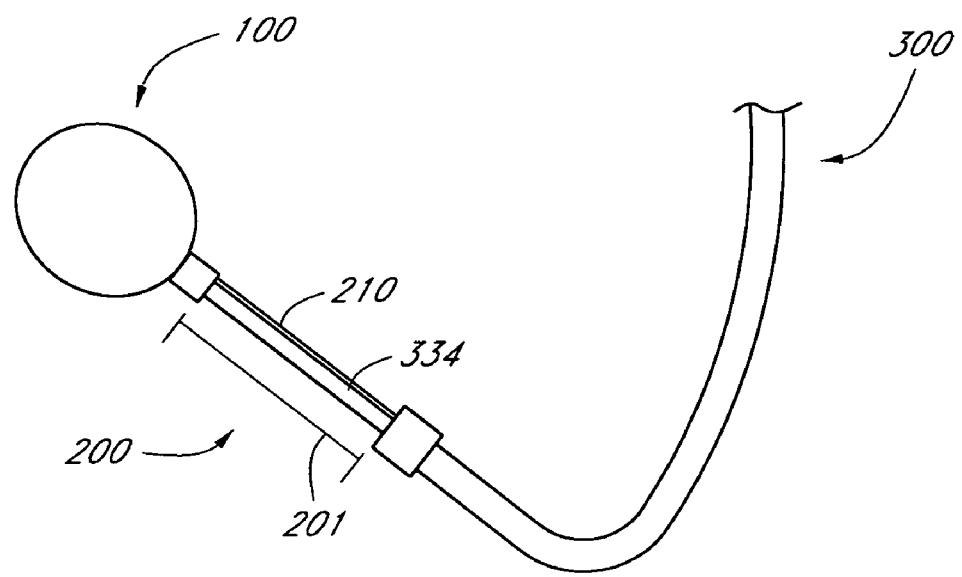
FIG. 3A is a side elevational view of the distal end of an embodiment of an implant delivery system.

FIG. 3A illustrates one example of an implant 100 coupled to a catheter system 300 with an implant release and recapture mechanism 200. In the illustrated embodiment, the implant release and recapture mechanism 200 is relatively stiff and extends over a release mechanism length 201. The implant release and recapture mechanism 200 includes an implant actuation shaft 334 and a tether line 210. The implant 100 is generally self-expandable and is held in a reduced-diameter configuration by pushing against the distal end of the inside of the implant 100 while pulling on the implant's proximal end. For example, the implant actuation shaft 334 pushes against the implant distal end while the tether line 210 is held in tension to maintain the implant 100 in a reduced-diameter configuration. To expand the implant, tension on the tether line 210 is reduced and/or the implant actuation shaft 334 is moved proximally.

However, the implant actuation shaft 334 and tether line 210 can have limited flexibility and can provide off-axis loading that creates moment arms and bending bias. Deployment of the implant 100 in the confines of the heart 5 (not illustrated here) may require bending of the implant release and recapture mechanism 200, a catheter system 300, but stiffness along a release mechanism length 201 reduces flexibility and creates moment arm and bending bias.

Figure 3B:
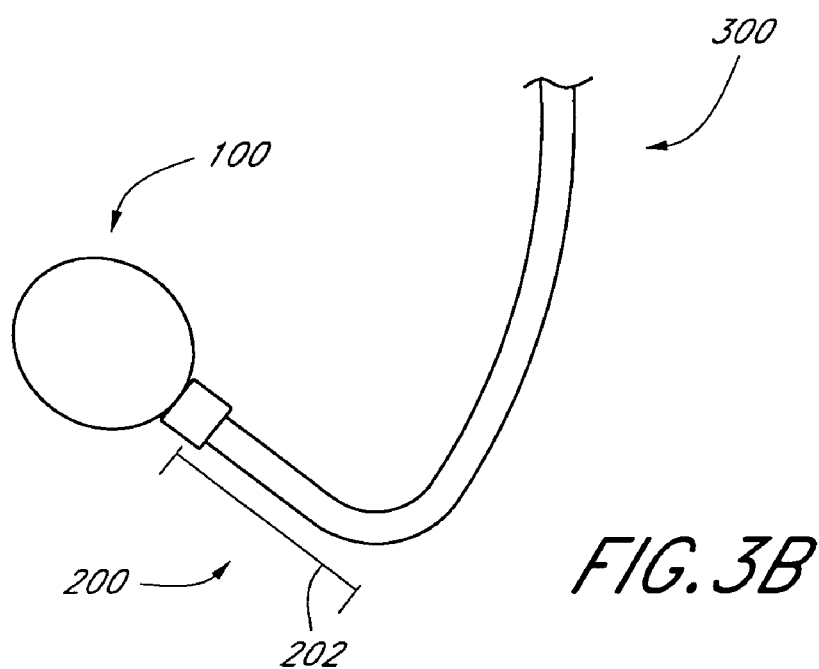
FIG. 3B is a side elevational view of the distal end of another embodiment of an implant delivery system.

FIG. 3B illustrates another embodiment of an implant 100 coupled to a catheter system 300 with an implant release and recapture mechanism 200. In the illustrated embodiment, the implant release and recapture mechanism 200 is relatively stiff and extends over a release mechanism length 202. The implant release and recapture mechanism 200 and the catheter system 300 are flexible and can be manipulated in order to access the LAA 10. When device stiffness or rigidity along a release mechanism length 202 is shorter than a release mechanism length 201, the device has increased flexibility and shorter moment arms, resulting in less bending bias.

FIGS. 4A-C illustrate the implant release sequence of the implant 100 with the implant release and recapture mechanism 200 of FIG. 3A. FIG. 4A illustrates an example of an implant 100, an implant release and recapture mechanism 200, and a catheter system 300 where the implant release and recapture mechanism 200 is relatively stiff and extends over a release mechanism length 201. FIG. 4B illustrates a catheter system 300 using an implant actuation shaft 334 and a tether line 210, which are used as components within the implant release and recapture mechanism 200. When the implant 100 is radially expanded the implant 100 can move axially toward the distal end of the implant 100. The off-axis tension in the tether line 210 can create moment arms and bending bias which can cause the implant 100 to "jump," move, rotate, etc., within the LAA 10 when the implant 100 is detached from the implant delivery system, as is illustrated in FIG. 4C.

FIGS. 5A-C illustrate the implant release sequence of the implant 100 with the implant release and recapture mechanism 200 of FIG. 3B. FIG. 5A illustrates an example of an implant 100, an implant release and recapture mechanism 200, a catheter system 300 where the implant release and recapture mechanism 200 is relatively stiff and extends over a release mechanism length 202. Length 202 is shorter than length 201 of FIG. 4A. FIG. 5B illustrates the expansion of the implant 100 with shorter moment arms and less bending bias than the systems illustrated in FIGS. 4A-C. As illustrated in FIG. 5C, the release of the implant 100 from the catheter system 300 results in smaller moment arms and less bending bias than in FIGS. 4A-C. The detachment of the implant 100 results in less of a "jump" and reduced movement and/or rotation within the LAA 10.

1. Implant

Figure 6:
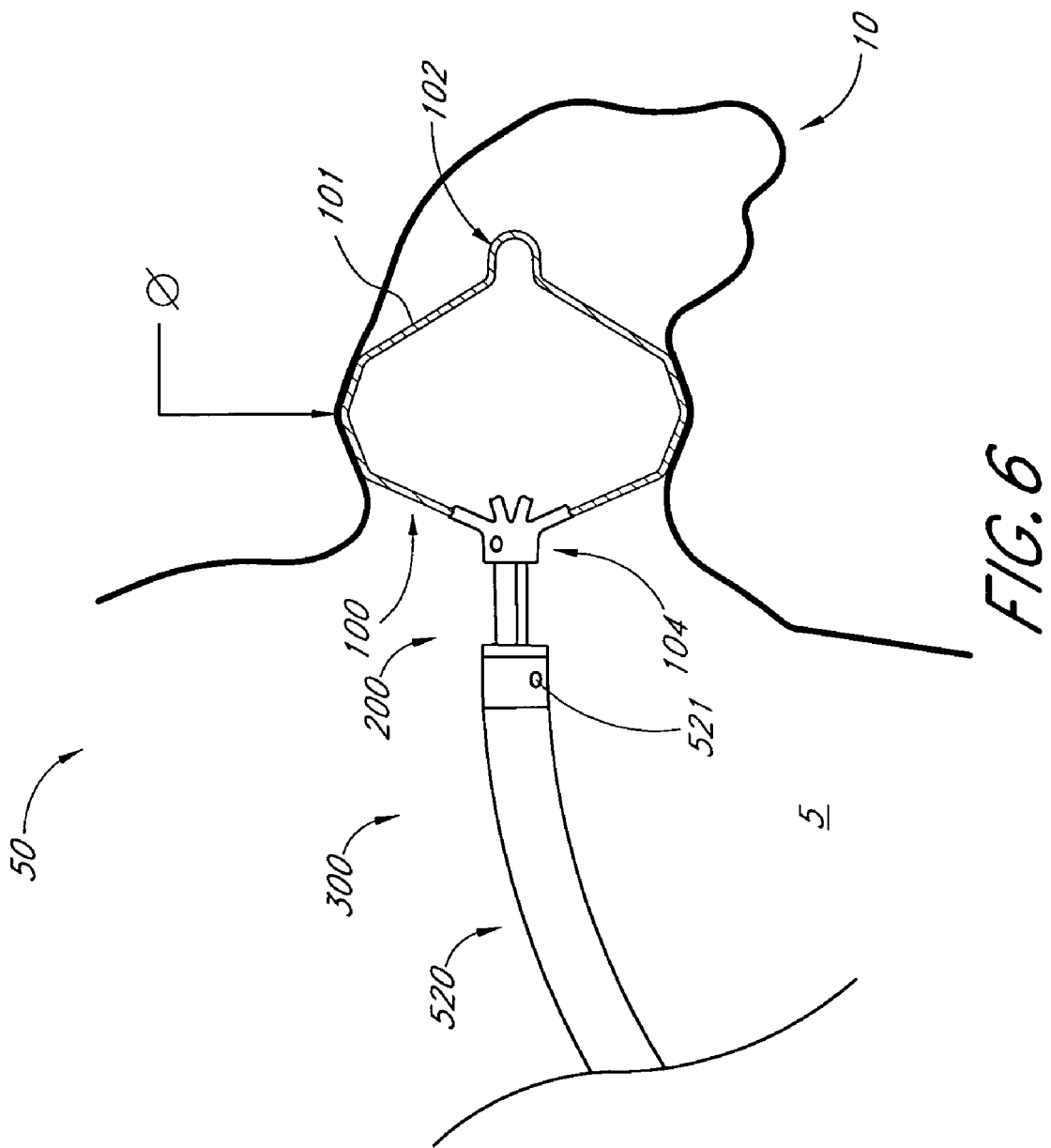
FIG. 6 is a schematic view of a deployment system delivering an implantable containment device to the left atrial appendage.

FIG. 6 illustrates an implant 100 placed inside a LAA 10 of a heart 5, an implant release and recapture mechanism 200, and a catheter system 300. In one embodiment, the implant 100 is a transluminally delivered device designed to occlude or contain particles within the LAA 10 and prevent thrombus from forming in, and emboli from originating from, the LAA 10. The delivery system 50 may be used to deliver the implant 100 to occlude or block the LAA 10 in a patient with atrial fibrillation. The delivery system 50 may be compatible for use with a transseptal sheath (not shown). The delivery system 50 and implant 100 may be selected to allow the implant 100 to be positioned, repositioned, and retrieved from the LAA 10 if necessary.

The implant 100 often includes a frame 101 and a membrane (not shown) on a proximal face 104 of the implant, such as described below. In an embodiment, the frame 101 is constructed of self-expanding nitinol supports. The membrane may be constructed of a fabric covering, such as one made of ePTFE, or an ePTFE/PE laminate. To attach the membrane to the frame 101, a PE mesh preferably is placed against the supports, with one sheet of ePTFE preferably placed over the PE mesh and another sheet of ePTFE preferably placed on an opposite side of the supports. The membrane may be heated on both sides causing the PE to melt into both sheets of ePTFE, thereby surrounding a portion of the frame 101. The nitinol supports allow the implant 100 to self-expand in the appendage 10, covering the orifice with the laminated fabric. The porous ePTFE/PE lamination facilitates rapid endothelialization and healing.

In one embodiment, the implant 100 is expandable and collapsible. The implant 100 can include anchors that extend from the implant's frame 101 when the implant 100 is expanded, as described below. The implant 100 is available in a range of sizes to accommodate the anatomy of a patient's LAA 10. When used in the LAA 10, the implant 100 may have an expanded diameter within the range of from about 1 cm to about 5 cm, and, in one embodiment, about 3 cm. The overall axial length of the implant 10 from its distal end 102 to its proximal end 104 is within the range of from about 1.5 cm to about 4 cm and, in one embodiment, about 2.5 cm.

In one embodiment, the delivery system 50 includes a transseptal sheath 520. A radiopaque marker 521 is located near the distal end of the transseptal sheath 520.

Figure 7B:
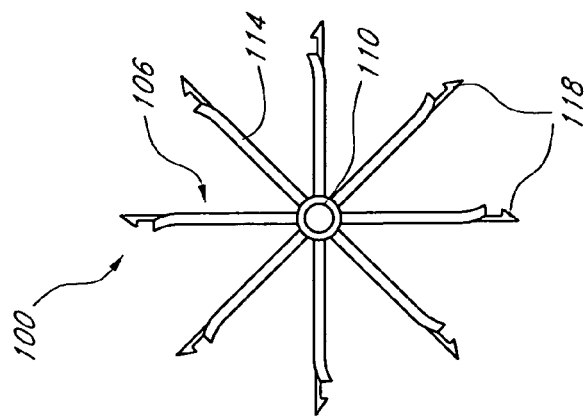
FIG. 7B is an end view taken along the line 7B-7B of FIG. 7A.
Figure 7A:
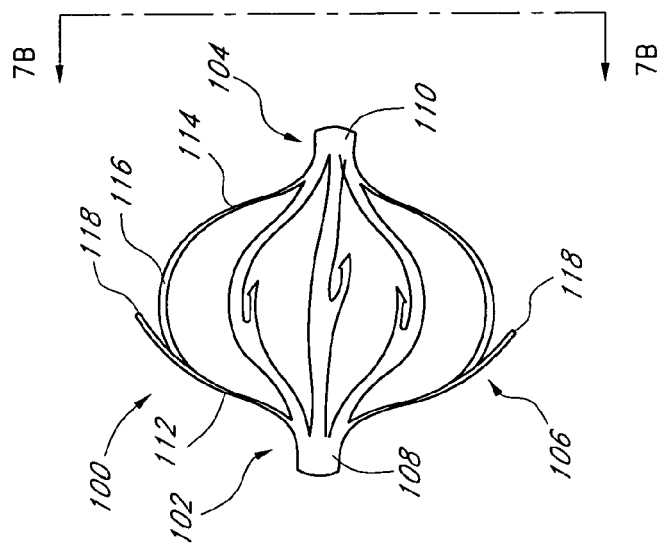
FIG. 7A is a side elevational view of the device of FIG. 7.
Figure 7:
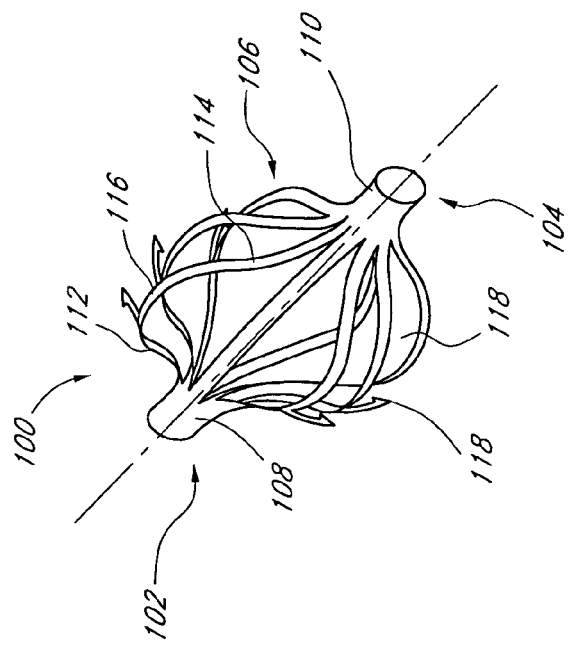
FIG. 7 is a perspective view of a support structure for a containment device in accordance with a further embodiment of the present invention.

FIGS. 7, 7A and 7B illustrate an implant 100 in accordance with another embodiment of the present invention. The implant 100 includes a distal end 102, a proximal end 104, and a longitudinal axis extending therebetween. A plurality of supports 106 extend between a distal hub 108 and a proximal hub 110. At least two or three supports 106 are provided, and in other embodiments, at least about ten supports 106 are provided. In one embodiment, sixteen supports 106 are provided. However, the precise number of supports 106 can be modified, depending upon the desired physical properties of the implant 100 as will be apparent to those of skill in the art in view of the disclosure herein, without departing from the present invention.

In an embodiment, each support 106 includes a distal spoke portion 112, a proximal spoke portion 114, and an apex 116. Each of the distal spoke portion 112, the proximal spoke portion 114, and the apex 116 may be a region on an integral support 106, such as a continuous rib or frame member which extends in a generally curved configuration as illustrated with a concavity facing towards the longitudinal axis of the implant 100. Thus, no distinct point or hinge at apex 116 is necessarily provided.

At least some of the supports 106, and, preferably, each support 106, is provided with one or two or more anchors 118 or barbs 118. In the illustrated configuration, the implant 100 is in its enlarged orientation, such as for occluding a left atrial appendage 10 or other body cavity or lumen. In this orientation, each of the barbs 118 projects generally radially outwardly from the longitudinal axis, and is inclined in the proximal direction. One or more barbs may also be inclined distally, as is discussed elsewhere herein. In an embodiment where the barbs 118 and corresponding support 106 are cut from a single ribbon, sheet or tube stock, the barb 118 will incline radially outwardly at approximately a tangent to the curve formed by the support 106.

The illustrated anchor 118 is in the form of a barb, with at least one on each support 106 for extending into tissue at or near the opening of the LAA 10. Depending upon the embodiment, two or three barbs 118 may alternatively be desired on each support 106. In the single barb 118 embodiment of FIG. 7, each barb 118 is inclined in a proximal direction. This is to inhibit proximal migration of the implant out of the left atrial appendage 10. In this context, distal refers to the direction into the left atrial appendage 10, and proximal refers to the direction from the left atrial appendage 10 into the heart 5.

Alternatively, one or more barbs 118 may face distally, to inhibit distal migration of the implant 100 deeper into the LAA 10. Thus, the implant 100 may be provided with at least one proximally facing barb 118 and at least one distally facing barb 118. For example, in an embodiment of the type illustrated in FIG. 10, discussed below, a proximal plurality of barbs 118 may be inclined in a first direction, and a distal plurality of barbs 118 may be inclined in a second direction, to anchor the implant 100 against both proximal and distal migration.

The implant 100 constructed from the frame illustrated in FIG. 7 may be constructed in any of a variety of ways, as will become apparent to those of skill in the art in view of the disclosure herein. In one method, the implant 100 is constructed by laser cutting a piece of tube stock to provide a plurality of axially extending slots in-between adjacent supports 106. Similarly, each barb 118 can be laser cut from the corresponding support 106 or space in-between adjacent supports 106. The generally axially extending slots which separate adjacent supports 106 end a sufficient distance from each of the proximal end 104 and distal end 102 to leave a proximal hub 110 and a distal hub 108 to which each of the supports 106 will attach. In this manner, an integral cage structure may be formed. Alternatively, each of the components of the cage structure may be separately formed and attached together such as through soldering, brazing, heat bonding, adhesives, and other fastening techniques which are known in the art.

A further method of manufacturing the implant 100 is to laser cut a slot pattern on a flat sheet of appropriate material, such as a flexible metal or polymer. The supports 106 may comprise a metal such as stainless steel, nitinol, Elgiloy, or others which can be determined through routine experimentation by those of skill in the art. Wires having a circular or rectangular cross-section may be utilized depending upon the manufacturing technique. In one embodiment, rectangular cross section spokes are cut such as by known laser cutting techniques from tube stock, a portion of which forms a proximal hub 110 or a distal hub 108. The flat sheet may thereafter be rolled about an axis and opposing edges bonded together to form a tubular structure.

The apex portion 116 which carries the barb 118 may be advanced from a low profile orientation in which each of the supports 106 extend generally parallel to the longitudinal axis, to an implanted orientation as illustrated, in which the apex 116 and the barb 118 are positioned radially outwardly from the longitudinal axis. The support 106 may be biased towards the enlarged orientation, or may be advanced to the enlarged orientation under positive force following positioning within the tubular anatomical structure, in any of a variety of manners.

Referring to FIGS. 8 and 9, the implant 100 may be provided with a barrier 120 such as a mesh or fabric. The barrier 120 may comprise any of a variety of materials which facilitate cellular in-growth, such as ePTFE. The suitability of alternate materials for barrier 120 can be determined through routine experimentation by those of skill in the art. The barrier 120 may be provided on either one or both axially facing sides of the implant 100. In one embodiment, the barrier 120 comprises two layers, with one layer on each side of a cage formed by a plurality of supports 106. The two layers may be bonded to each other around the supports 106 in any of a variety of ways, such as by heat bonding with or without an intermediate bonding layer such as polyethylene or FEP, adhesives, sutures, and other techniques which will be apparent to those of skill in the art in view of the disclosure herein. In an embodiment, the barrier 120 has a thickness of no more than about 0.003" and a porosity within the range of from about 5 μm to about 60 μm.

Barrier 120 may be provided on only one hemisphere, proximal face 122, or may be carried by the entire implant 100 from proximal end 104 to distal end 102. The barrier may be secured to the radially inwardly facing surface of the supports 106, as illustrated in FIG. 9, or may be provided on the radially outwardly facing surfaces of supports 106, or both.

A further embodiment of the implant 100 is illustrated in FIG. 10, in which the apex 116 is elongated in an axial direction to provide additional contact area between the implant 100 and the wall of the tubular structure. In this embodiment, one or two or three or more anchors 118 may be provided on each support 106, depending upon the desired clinical performance. The implant 100 illustrated in FIG. 10 may also be provided with any of a variety of other features discussed herein, such as a partial or complete barrier 120. In addition, the implant 100 illustrated in FIG. 10 may be enlarged using any of the techniques disclosed elsewhere herein.

Figure 11:
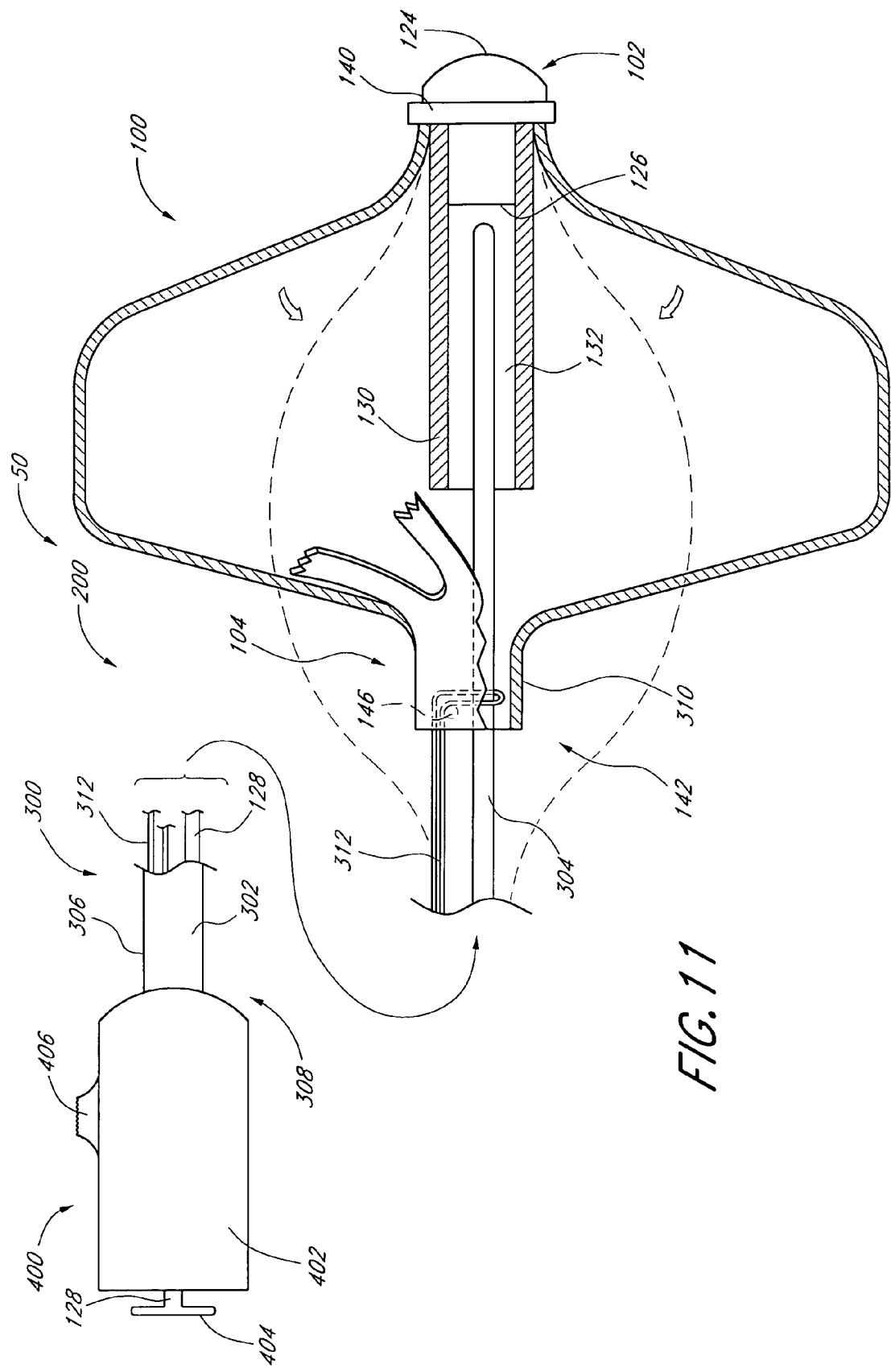
FIG. 11 is a schematic view of a deployment system in accordance with one embodiment of the present invention.

FIG. 11 illustrates another embodiment of the present invention. The implant 100 may be in the form of any of those described previously herein, as modified below. In general, the implant 100 is movable from a reduced crossing profile to an enlarged crossing profile. The implant 100 is generally introduced into the body in its reduced crossing profile, and when positioned at the desired deployment location, the implant 100 is expanded to its enlarged crossing profile. When expanded, the implant 100 obstructs or filters the flow of desired particles, emboli, blood, etc., or performs other functions while positioned therein.

The implant 100 may be biased in the direction of the enlarged crossing profile, may be neutrally biased, or may be biased in the direction of the reduced crossing profile. Any modifications to the device and deployment system to accommodate these various aspects of the implant 100 may be readily accomplished by those of skill in the art in view of the disclosure herein.

The implant 100 is a detachable component of an adjustable implant delivery system 50. The implant deliver system 50 generally includes a catheter 302 for inserting in implant into a patient's vasculature, advancing it percutaneously through the vasculature, positioning it at a desire deployment location, and deploying the implant 100 at the deployment location, such as within a body cavity or lumen, as discussed above. The catheter 302 generally includes an elongate flexible tubular body 306 that extends between a proximal end 308 and a distal end 310. The catheter body has a sufficient length and diameter to permit percutaneous entry into the vascular system and transluminal advancement through the vascular system to the desired deployment site.

For example, in an embodiment intended for access at the femoral vein and deployment within the left atrial appendage 50, the catheter 302 has a length within the range of from about 50 cm to about 150 cm, and a diameter of generally no more than about 15 French. Further dimensions and physical characteristics of catheters for navigation to particular sites within the body are well understood in the art and will not be further described herein.

The tubular body 306 is further provided with a handle 402 generally on the proximal end 308 of the catheter 302. The handle 402 permits manipulation of the various aspects of the implant delivery system 50, as will be discussed below. Handle 402 may be manufactured in any of a variety of ways, typically by injection molding or otherwise forming a handpiece for single-hand operation, using materials and construction techniques well known in the medical device arts.

In the illustrated embodiment, the distal end 102 of the implant 100 is provided with an implant plug 124. Implant plug 124 provides a stopping surface 126 for contacting an axially movable core 304. The core 304 extends axially throughout the length of the catheter body 302, and is attached at its proximal end to a core control 404 on the handle 402. In some embodiments, the axially movable core is referred to as a drive shaft. In one embodiment, the implant plug 124 comprises an a traumatic tip, such that contact between the a traumatic tip and the inside surface of the LAA 10 does not cause significant damage to the LAA 10.

The core 304 may comprise any of a variety of structures which has sufficient lateral flexibility to permit navigation of the vascular system, and sufficient axial column strength to enable reduction of the implant 100 to its reduced crossing profile. Any of a variety of structures such as hypotube, solid core wire, "bottomed out" coil spring structures, or combinations thereof may be used, depending upon the desired performance of the finished device. In one embodiment, the core 304 comprises stainless steel tubing.

The distal end of core 304 is positioned within a recess, cavity or lumen 132 defined by a proximally extending distal guide tube 130. In the illustrated embodiment, the distal guide tube 130 is a section of tubing such as metal hypotube, which is attached at the distal end 102 of the implant and extends proximally within the implant 100. The distal guide tube 130 preferably extends a sufficient distance in the proximal direction to inhibit buckling or prolapse of the core 304 when distal pressure is applied to the core control 404 to reduce the profile of the implant 100. However, the guide tube 130 should not extend proximally a sufficient distance to interfere with the opening of the implant 100.

As will be appreciated by reference to FIG. 11, the guide tube 130 may operate as a limit on distal axial advancement of the proximal end 104 of implant 100. Thus, the guide tube 130 preferably does not extend sufficiently far proximally from the distal end 102 to interfere with optimal opening of the implant 100. The specific dimensions are therefore relative, and will be optimized to suit a particular intended application. In one embodiment, the implant 100 has an implanted outside diameter within the range of from about 5 mm to about 45 mm, and an axial implanted length within the range of from about 5 mm to about 45 mm. The guide tube 130 has an overall length of about 3 mm to about 35 mm, and an outside diameter of about 0.095 inches.

2. Implant Release and Recapture Mechanisms

Various embodiments of implant release and recapture mechanisms provide an interface between an implant and a catheter system used to deploy, detach, and recapture the implant.

a. Pull Wire Mechanisms

Referring back to FIG. 11, there is illustrated an embodiment of an implant delivery system 50 with a detachable implant 100, an implant release and recapture mechanism 200, a catheter system 300, and a deployment handle 400. As illustrated in this embodiment, the implant release and recapture mechanism 200 includes a release element, such as a pull wire 312, which keeps the proximal end 104 of the implant 100 in tension. An axially moveable core 304 simultaneously pushes against the distal end 102 of the implant 100. The combination of pulling on the implant proximal end 104 while pushing on its distal end 102 keeps the implant 100 in a compressed state. When either the core 304 is pulled proximally or the pull wire 312 is allowed to move distally, the tension on the ends of the implant 100 is reduced, thereby allowing the spring loaded or shape memory material in the implant 100 to radially expand into its normal expanded state.

In this embodiment, the proximal end 104 of the implant 100 is provided with a releasable lock 142 for attachment to a pull wire 312. Pull wire 312 extends proximally throughout the length of the tubular body 306 to a proximal pull wire control 406 on the handle 402.

As used herein, the term pull wire is intended to include any of a wide variety of structures which are capable of transmitting axial tension or compression such as a pushing or pulling force with or without rotation from the proximal end 308 to the distal end 310 of the catheter 302. Thus, monofilament or multifilament metal or polymeric rods or wires, woven or braided structures may be utilized. Alternatively, tubular elements such as a concentric tube positioned within the outer tubular body 306 may also be used as will be apparent to those of skill in the art.

In the illustrated embodiment in FIG. 11, the pull wire 312 is releasably connected to the proximal end 104 of the implant 100. This permits proximal advancement of the proximal end of the implant 100, which cooperates with a distal retention force provided by the core 304 against the distal end of the implant to axially elongate the implant 100 thereby reducing it from its implanted configuration to its reduced profile for implantation. The proximal end of the pull wire 312 may be connected to any of a variety of pull wire controls 406, including rotational knobs, levers and slider switches, depending upon the design preference.

The implant delivery system 50 thus permits the implant 100 to be maintained in a low crossing profile configuration, to enable transluminal navigation to a deployment site. Following positioning at or about the desired deployment site, proximal retraction of the core 304 enables the implant 100 to radially enlarge under its own bias to fit the surrounding tissue structure. Alternatively, the implant can be enlarged under positive force, such as by inflation of a balloon or by a mechanical mechanism. Once the clinician is satisfied with the position of the implant 100, such as by injection of dye and visualization using conventional techniques, the core 304 is proximally retracted thereby releasing the lock 142 and enabling detachment of the implant 100 from the deployment system 300.

If, however, visualization reveals that the implant 100 is not at the location desired by the clinician, proximal retraction of the pull wire 312 with respect to the core 304 will radially reduce the diameter of the implant 100, thereby enabling repositioning of the implant 100 at the desired site. Thus, the present invention permits the implant 100 to be enlarged or reduced by the clinician to permit repositioning and/or removal of the implant 100 as may be desired.

b. Threadable Torque Rod Mechanisms

Figure 12:
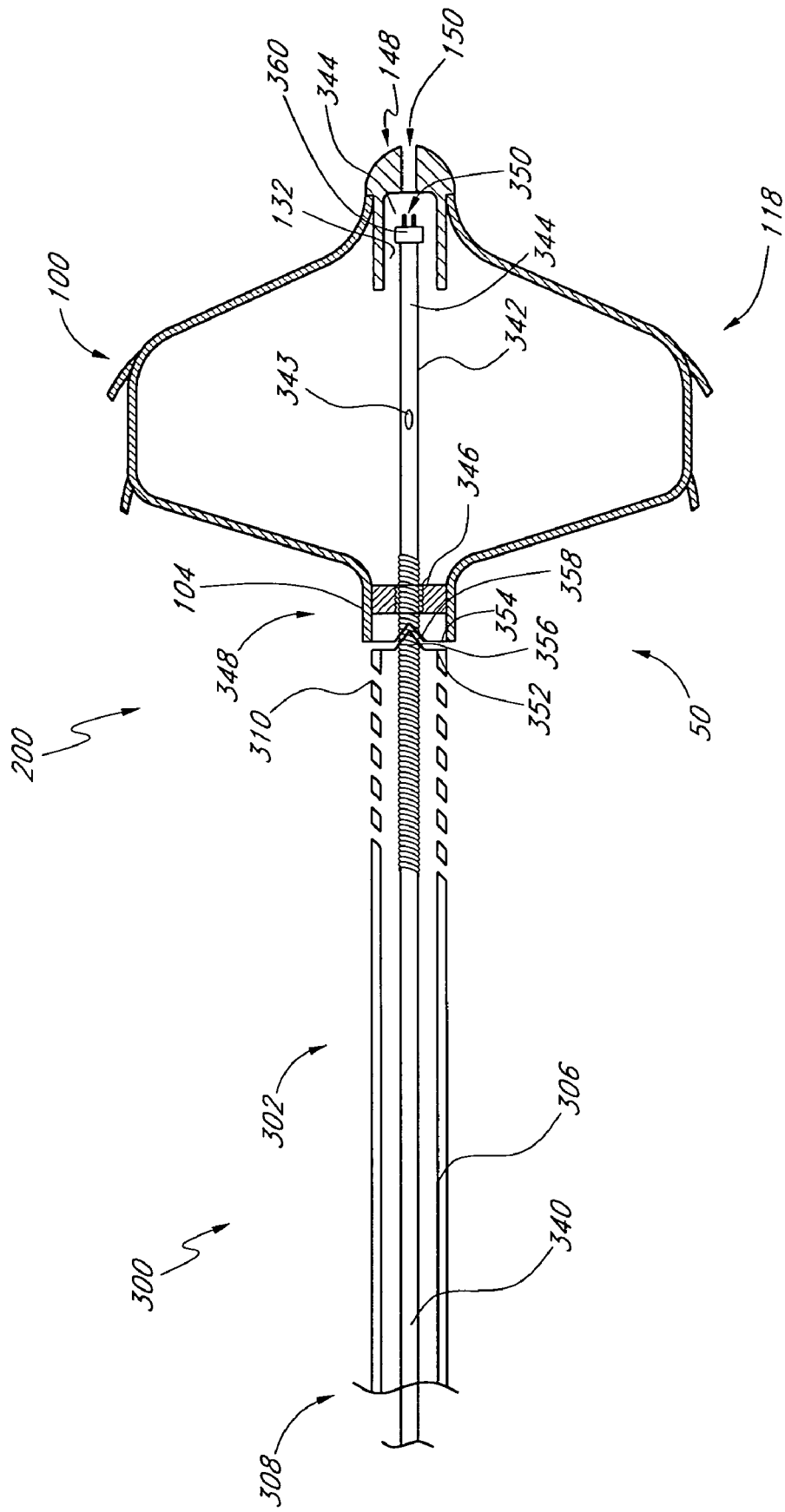
FIG. 12 is a schematic view of an alternate deployment system in accordance with one embodiment of the present invention.

FIG. 12 illustrates an alternate embodiment of an implant deployment system 50 in which an implant 100 is radially enlarged or reduced by rotating a torque element extending throughout the deployment catheter. The elongate flexible tubular body 306 of the deployment catheter 302 includes a rotatable torque rod 340 extending axially therethrough. The proximal end of the torque rod 340 may be connected at a proximal manifold to a manual rotation device such as a hand crank, thumb wheel, rotatable knob or the like. Alternatively, the torque rod 340 may be connected to a power driven source of rotational energy such as a motor drive or air turbine. The distal end of the torque rod 340 is integral with or is connected to a rotatable core 342 which extends axially through the implant 100. A distal end 344 of the rotatable core 342 is positioned within a cavity 132 as has been discussed.

The terms torque rod or torque element are intended to include any of a wide variety of structures which are capable of transmitting a rotational torque throughout the length of a catheter body. For example, solid core elements such as stainless steel, nitinol or other nickel titanium alloys, or polymeric materials may be utilized. In an embodiment intended for implantation over a guidewire, the torque rod 340 is preferably provided with an axially extending central guidewire lumen. This may be accomplished by constructing the torque rod 340 from a section of hypodermic needle tubing, having an inside diameter of from about 0.001 inches to about 0.005 inches or more greater than the outside diameter of the intended guidewire. Tubular torque rods 340 may also be fabricated or constructed utilizing any of a wide variety of polymeric constructions which include woven or braided reinforcing layers in the wall. Torque transmitting tubes and their methods of construction are well understood in the intracranial access and rotational atherectomy catheter arts, among others, and are not described in greater detail herein.

Use of a tubular torque rod 340 also provides a convenient infusion lumen for injection of contrast media within the implant 100, such as through a port 343 or lumen 350. In one embodiment, axially moveable core 304 also includes a lumen 350. The lumen 350 preferably allows visualization dye to flow through the lumen 350 of the axially moveable core 304, through the lumen 150 of the implant end cap 148, and into the left atrial appendage 10. Such usage of visualization dye is useful for clinical diagnosis and testing of the position of the implant 100 within the left atrial appendage 10 or other body opening, as described in greater detail below.

The marker 360 as shown in FIG. 12 advantageously assists in locating the position of the distal end 344 of the axially moveable core 342. In one embodiment, marker 360 comprises a radiopaque band press fit onto the distal end 344 of the axially moveable core 342. Marker 360 preferably is made from a material readily identified after insertion into a patient's body by using visualization techniques that are well known to those of skill in the art. In one embodiment, the marker 360 is made from gold, or tungsten, or any such suitable material, as is well known to those of skill in the art. In another embodiment, marker 360 is welded, soldered, or glued onto the distal end 344 of the axially moveable core 342. In one embodiment, marker 360 is an annular band and surrounds the circumference of the axially moveable core 342. In other embodiments, the marker 360 does not surround the circumference of the axially moveable core 342. In other embodiments, marker 360 includes evenly or unevenly spaced marker segments. In one embodiment, the use of marker segments is useful to discern the radial orientation of the implant 100 within the body.

The proximal end 104 of the implant 100 is provided with a threaded aperture 346 through which the core 342 is threadably engaged. As will be appreciated by those of skill in the art in view of the disclosure herein, rotation of the threaded core 342 in a first direction relative to the proximal end 104 of the implant 100 will cause the rotatable core 342 to advance distally. This distal advancement will result in an axial elongation and radial reduction of the implantable device 100. Rotation of the rotatable core 342 in a reverse direction will cause a proximal retraction of the rotatable core 342, thus enabling a radial enlargement and axial shortening of the implantable device 100.

The deployment catheter 302 is further provided with an anti-rotation lock 348 between a distal end 310 of the tubular body 306 and the proximal end 104 of the implant 100. In general, the rotational lock 348 may be conveniently provided by cooperation between a first surface 352 on the distal end 310 of the deployment catheter 302, which engages a second surface 354 on the proximal end 104 of the implant 100, to rotationally link the deployment catheter 302 and the implantable device 100. Any of a variety of complementary surface structures may be provided, such as an axial extension on one of the first 352 and second surfaces 354 for coupling with a corresponding recess on the other of the first 352 and second surfaces 354. Such extensions and recesses may be positioned laterally offset from the axis of the catheter 302. Alternatively, they may be provided on the longitudinal axis with any of a variety of axially releasable anti-rotational couplings having at least one flat such as a hexagonal or other multifaceted cross-sectional configuration.

Upon placement of the implant 100 at the desired implantation site, the torque rod 340 is rotated in a direction that produces an axial proximal retraction. This allows radial enlargement of the radially outwardly biased implant 100 at the implantation site. Continued rotation of the torque rod 340 will cause the threaded core 342 to exit proximally through the threaded aperture 346. At that point, the deployment catheter 302 may be proximally retracted from the patient, leaving the implanted device 100 in place.

By modification of the decoupling mechanism to allow the core 342 to be decoupled from the torque rod 340, the rotatable core 342 may be left within the implant 100, as may be desired depending upon the intended deployment mechanism. For example, the distal end of the core 342 may be rotatably locked within the end cap 148, such as by including complimentary radially outwardly or inwardly extending flanges and grooves on the distal end of the core 342 and inside surface of the cavity 132. In this manner, proximal retraction of the core 342 by rotation thereof relative to the implant 100 will pull the end cap 148 in a proximal direction under positive force. This may be desirable as a supplement to or instead of a radially enlarging bias built into the implant 100.

In other embodiments, the torque rod 340 is threaded at its distal end. The distal end is threaded into a sliding nut located within a guide tube extending from the distal end of the implant 100. Such embodiments are described in greater detail in U.S. application Ser. No. 10/642,384, filed Aug. 15, 2003, published as U.S. Publication No. 2005/0038470, which is expressly incorporated by reference herein.

Figure 13A:
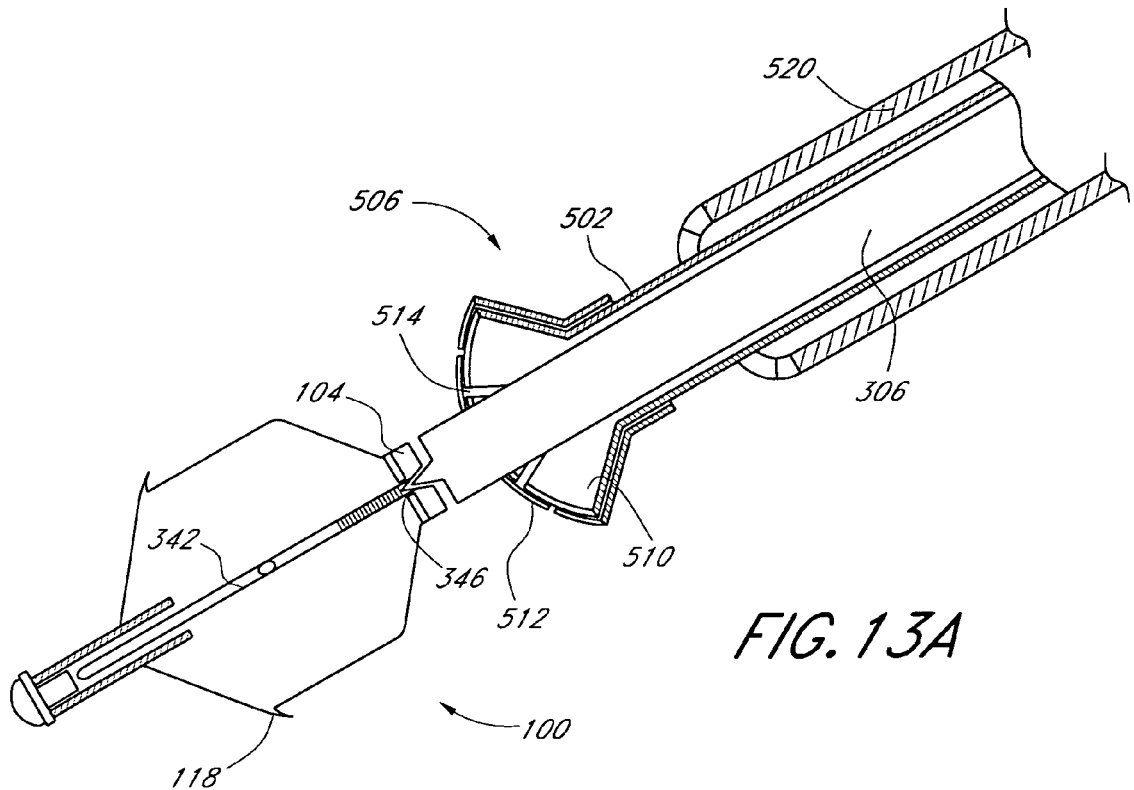
FIG. 13A illustrates a schematic cross-sectional view through the distal end of a retrival catheter having a containment device removably connected thereto in accordance with one embodiment of the present invention.

The implant 100 may also be retrieved and removed from the body in accordance with a further aspect of the present invention. One manner of retrieval and removal is described with respect to FIGS. 13A-E. Referring to FIG. 13A, an implanted device 100 is illustrated as releasably coupled to the distal end of the tubular body 306, as has been previously discussed. Coupling may be accomplished by aligning the tubular body 306 with the proximal end 104 of the deployed implant 100, under fluoroscopic visualization, and distally advancing a rotatable core 342 through the threaded aperture 346. Threadable engagement between the rotatable core 342 and aperture 346 may thereafter be achieved, and distal advancement of core 342 will axially elongate and radially reduce the implant 100.

The tubular body 306 is axially movably positioned within an outer tubular delivery or retrieval catheter 502. In various embodiments, the retrieval catheter 502 may be separate and distinct from the delivery or deployment catheter 302, or the retrieval catheter 502 may be coaxial with the delivery or deployment catheter 302, or the retrieval catheter 502 may be the same catheter as the delivery or deployment catheter 302. Catheter 502 extends from a proximal end (not illustrated) to a distal end 506. The distal end 506 is preferably provided with a flared opening, such as by constructing a plurality of petals 510 for facilitating proximal retraction of the implant 100 as will become apparent.

Petals 510 may be constructed in a variety of ways, such as by providing axially extending slits in the distal end 506 of the catheter 502. In this manner, preferably at least about three, and generally at least about four or five or six petals or more will be provided on the distal end 506 of the catheter 502. Petals 510 manufactured in this manner would reside in a first plane, transverse to the longitudinal axis of the catheter 502, if each of such petals 510 were inclined at 90 degrees to the longitudinal axis of the catheter 502.

Figure 13B:
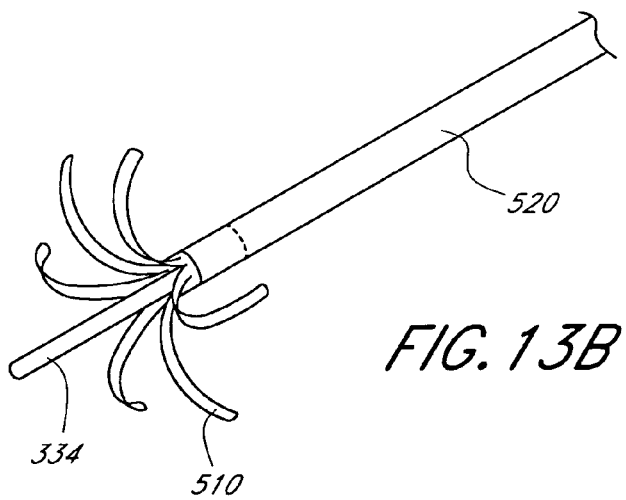
FIG. 13B is a perspective view of an embodiment of a single layer petal configuration of a portion of a retrieval catheter in accordance with one embodiment of the present invention.

In one embodiment, a second layer of petals 512 are provided, which would lie in a second, adjacent plane if the petals 512 were inclined at 90 degrees to the longitudinal axis of the catheter 502. Preferably, the second plane of petals 512 is rotationally offset from the first plane of petals 510, such that the second petals 512 cover the spaces 514 formed between each adjacent pair of petals 510. The use of two or more layers of staggered petals 510 and 512 has been found to be useful in retrieving implants 100, particularly when the implant 100 carries a plurality of tissue anchors 118. However, in many embodiments, the retrieval catheter 502 includes only a single plane of petals 510, such as illustrated in FIG. 13B.

The petals 510 and 512 may be manufactured from any of a variety of polymer materials useful in constructing medical device components such as the catheter 502. This includes, for example, polyethylene, PET, PEEK, PEBAX, and others well known in the art. The second petals 512 may be constructed in any of a variety of ways. In one convenient construction, a section of tubing which concentrically fits over the catheter 502 is provided with a plurality of axially extending slots in the same manner as discussed above. The tubing with a slotted distal end may be concentrically positioned on the catheter 502, and rotated such that the space between adjacent petals 512 is offset from the space between adjacent petals 510. The hub of the petals 512 may thereafter be bonded to the catheter 502, such as by heat shrinking, adhesives, or other bonding techniques known in the art. FIG. 13B shows a perspective view of an embodiment of a single layer of petals 510 which is coaxial with a transseptal catheter 520 and an implant actuation shaft 334. The implant actuation shaft 334 can be rotatable core 342 as illustrated in FIG. 13A.

Figure 13C:
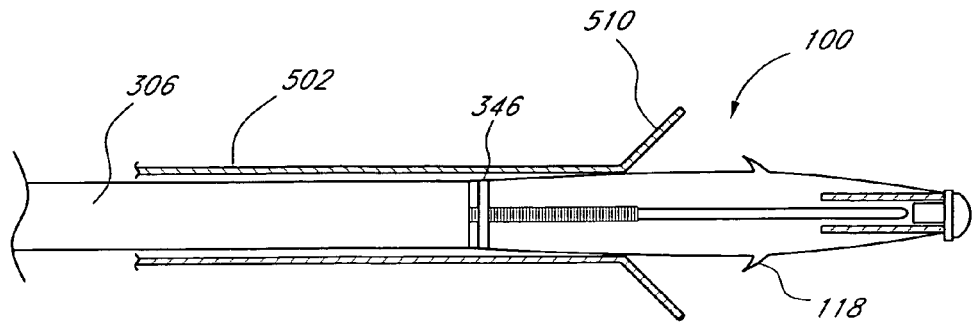
FIG. 13C is a schematic cross-sectional view of the system illustrated in FIG. 13A, with the containment device axially elongated and radially reduced.
Figure 13D:
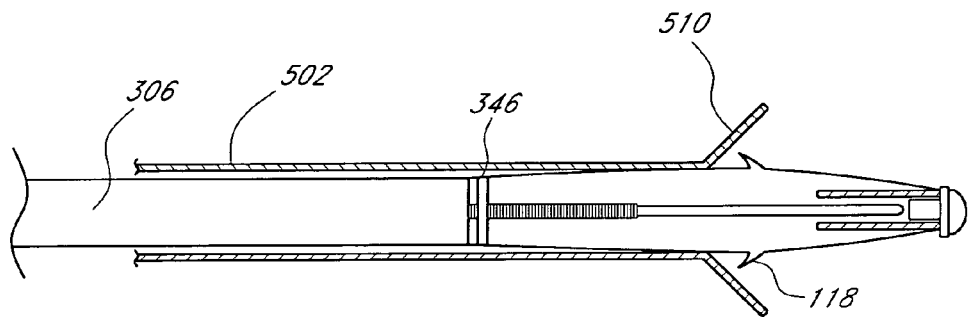
FIG. 13D is a cross-sectional schematic view as in FIG. 13C, with the containment device drawn part way into the retrieval catheter.
Figure 13E:
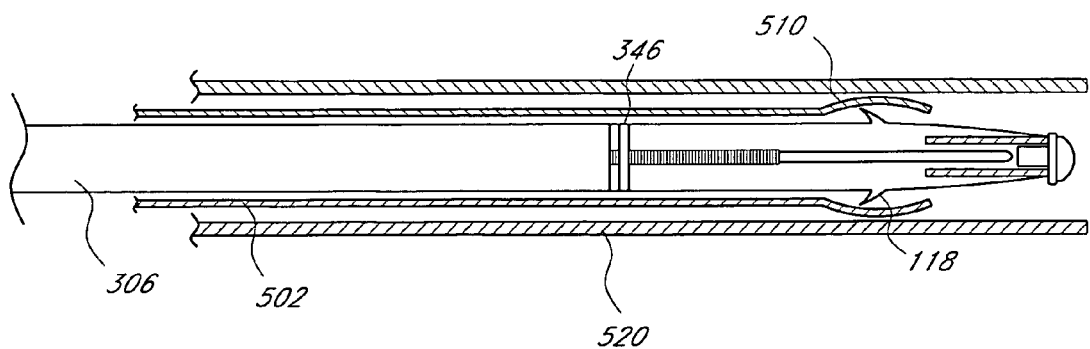
FIG. 13E is a schematic view as in FIG. 13D, with the containment device and delivery catheter drawn into a transseptal sheath.

The removal sequence will be further understood by reference to FIGS. 13C through 13E. Referring to FIG. 13C, the radially reduced implant 100 is proximally retracted part way into the retrieval catheter 502. This can be accomplished by proximally retracting the tubular body 306 and/or distally advancing the catheter 502. As illustrated in FIG. 13D, the tubular body 306 having the implant 100 attached thereto is proximally retracted a sufficient distance to position the tissue anchors 118 within the petals 510. The entire assembly of the tubular body 306, within the retrieval catheter 502 may then be proximally retracted within the transseptal sheath 520 or other tubular body as illustrated in FIG. 13E. The collapsed petals 510 allow this to occur while preventing engagement of the tissue anchors 118 with the distal end of the transseptal sheath 520 or body tissue. The entire assembly having the implant 100 contained therein may thereafter be proximally withdrawn from or repositioned within the patient.

The implant 100 may also be retrieved and removed from the body in accordance with a further aspect of the present invention. In various embodiments, a retrieval catheter system 500 may be separate and distinct from a delivery or deployment catheter system 300, or the catheter system 500 may be coaxial with the delivery or deployment catheter system 300, or the retrieval catheter system 500 may be part of the same catheter as the delivery or deployment catheter system 300. In embodiments where a retrieval catheter system 500 is connected or attached to a deployment catheter 302, overall system flexibility may be increased by the removal of an additional sheath or tube layer that would be required when a retrieval catheter 502 is coaxial with a deployment catheter 302.

Figure 14A:
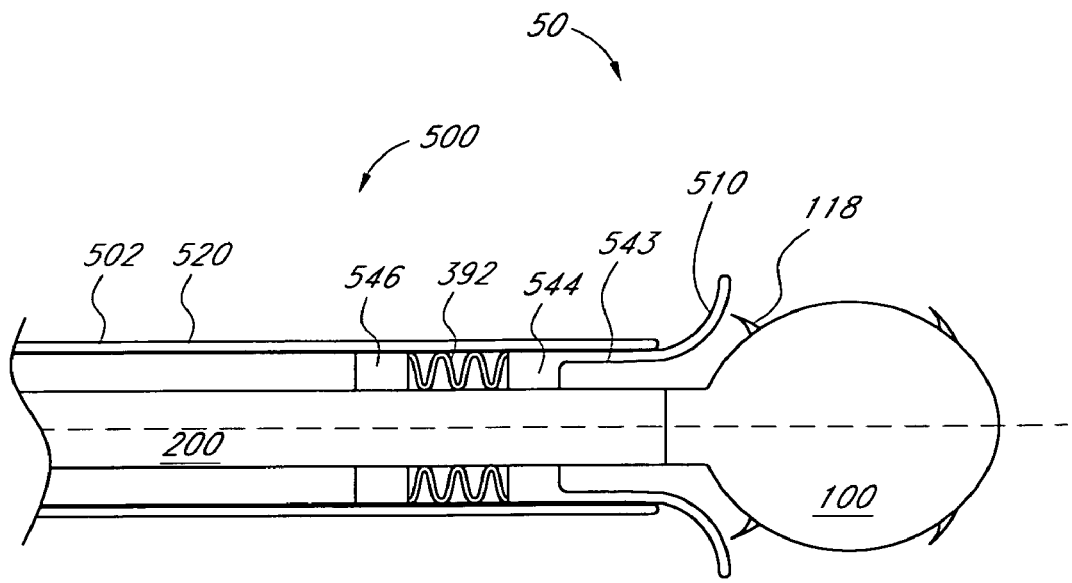
FIG. 14A illustrates a schematic cross sectional view through the distal end of a retrival system with a retrieval catheter and a mesh sock having a retrieval device removably connected to an implant in accordance with one embodiment of the present invention.
Figure 14B:
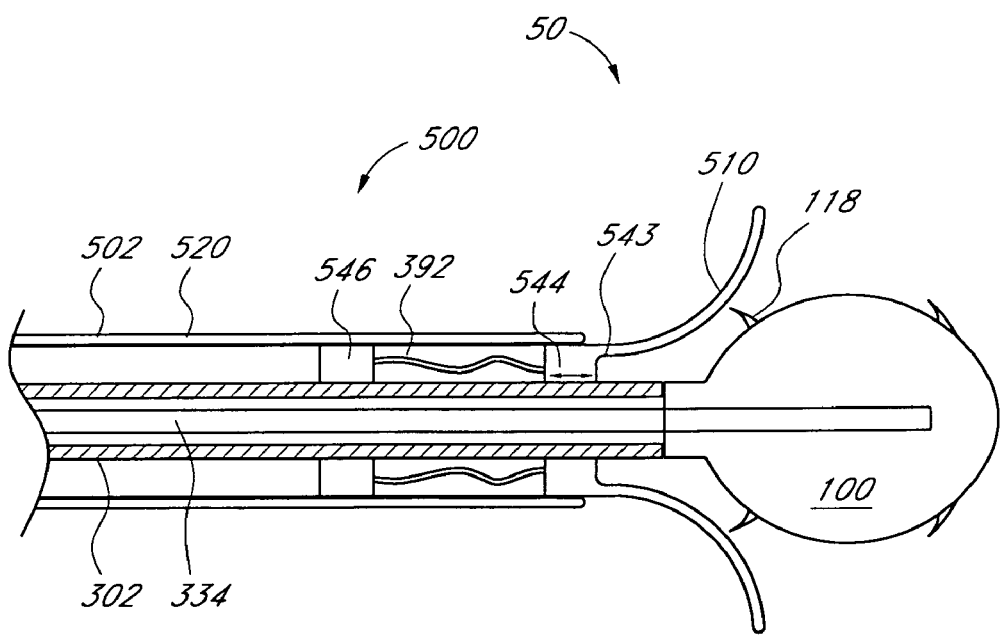
FIG. 14B is a cross sectional schematic view as in FIG. 14A with the retrieval catheter withdrawn proximally to release petals on the retrieval device.

FIGS. 14A-14B illustrate another embodiment of implant retrieval and removal. The retrieval catheter system 500 attaches near the distal end of an implant release and recapture mechanism 200. One advantage of these integral embodiments is an overall increase in system flexibility. Overall flexibility is increased because the system uses fewer sheathes or tubes. For example, the illustrated embodiment does not include an outer sheath or recapture catheter 502 (as described above in FIGS. 13A-13E) that extends all the way from the catheter distal end to its proximal end. Instead, a recapture section 543 is provided only at the distal end of the delivery system 50, as discussed below.

The integral recapture section 543 allows the recapture mechanism to be invisible to user until needed, thus eliminating the extra preparation and manipulation steps of a delivery system 50 having a separate recapture shaft 502 such as described above. These embodiments of the retrieval catheter system 500 may be used in conjunction with any of the embodiments of an implant release and recapture mechanism 200 disclosed herein or in other patents and applications incorporated by reference.

During retrieval, certain embodiments of the implant release and recapture mechanism 200 engage the implant 100 in order to radially-reduce the implant 100, as described above. Once the implant 100 is reduced to its radially-reduced configuration within the LAA 10, the system 50 with the implant 100 attached can be withdrawn proximally out of the LAA 10. In order to complete the recapture of the implant 100, the implant 100 can be withdrawn into the retrieval catheter system 500 in order to prevent damage to the heart 5 (not pictured here) and the rest of the body by an exposed implant.

The retrieval catheter system 500 may be used in conjunction with an implant release and recapture mechanism 200 and an implant 100 located within a LAA 10. One embodiment of a retrieval catheter system 500 uses a transseptal sheath 520 as a retrieval catheter 502 in actuating and performing parts of the recapture of an implant 100 into an implant delivery system 50. Instead of using a separate retrieval catheter as in some of the earlier embodiments, the retrieval catheter 502 of this embodiment is also the transseptal sheath 520. The transseptal sheath 520 may be described as a retrieval catheter or retrieval sheath 502 in FIGS. 14A through 151. In other embodiments, the retrieval sheath 502 may be any other catheter or tube used in conjunction with an implant deployment system 50.

As illustrated in FIGS. 14A-14B, a retrieval catheter system 500 works in conjunction with an implant release and recapture mechanism 200, a sock attachment section 546, a mesh sock 392, and a recapture section 543 with a plurality of petals 510 for facilitating proximal retraction of an implant 100. The mesh sock 392 is attached at its proximal end to a sock attachment section 546, and the mesh sock 392 is attached at its distal end to a recapture section 543 with a plurality of petals 510.

Various embodiments of suitable implant release and recapture mechanisms 200 are discussed in further detail in the U.S. application Ser. No. 11/607,253, filed Dec. 1, 2006, titled "METHOD AND APPARATUS FOR DELIVERING AN IMPLANT WITHOUT BIAS TO A LEFT ATRIAL APPENDAGE," which is incorporated by reference herein.

The recapture section 543 is slideably engageable with the outer surface of a catheter in an implant release and recapture mechanism 200. In FIG. 14B, the catheter is a deployment catheter 302. As shown in FIG. 14B, the recapture section 543 includes recapture flares 510 that are biased to move radially outwardly when extended past the distal end of the outer sheath 520. Returning to FIG. 14A, the recapture flares 510 are deployed around a collapsed implant 100 to buffer and protect the transseptal sheath 520 lumen from potential damage from implant anchors 118. The implant 100 may be brought to a position within the recapture flares 510 by moving the implant release and recapture mechanism 200 with the implant 100 proximally into the flares 510. The flares can be part of a separate recapture sheath that is maintained proximal to the distal end of the transseptal sheath 520 until used. In one embodiment the recapture section 543 is in the range of about 10 cm to about 15 cm long, and includes a tubular recapture section sheath portion 544 (e.g., a sheath portion) and a slotted tubular sheath portion which forms flares 510 (e.g., a flared portion).

The recapture section sheath portion 544 of the recapture section 543 may be a continuous tube, ring, or cylinder surrounding the deployment catheter 302 which may slide axially along the longitudinal axis of the catheter 302. The distal end of the recapture section 543 is preferably provided with a flared opening, such as by constructing a plurality of petals 510 for facilitating proximal retraction of the implant 100 as discussed above. Petals 510 may be constructed in a variety of ways, such as by providing axially extending slits directly into the distal end of a catheter in an implant release and recapture mechanism 200.

In other embodiments, a mesh sock 392 may be interposed between the recapture section 543 and a catheter in an implant release and recapture mechanism 200. The length of the petals 510 can be varied to cover the length of the implant 100 to sufficiently enclose implant barbs or anchors 118 on the implant 100. As illustrated in FIGS. 14A-15I, the petals cover the first proximal row of anchors 118. Covering the first row of anchors may be sufficient to collapse and retrieve an implant 100; however, it is possible to use longer petal 510 lengths that sufficiently cover all rows of anchors 118 on the implant 100 or cover the entire length of a radially-reduced implant 100.

At least about three, and generally at least about four or five or six petals or more are provided on the distal end of the recapture section 543. Petals 510 provided in this manner reside in a first plane, transverse to the longitudinal axis of the recapture section 543, if each of such petals 510 were inclined at 90 degrees to the longitudinal axis of the recapture section 543.

In another embodiment, a second layer of petals 512 are provided (as in FIG. 13A), which lie in a second, adjacent plane if the petals 512 were inclined at 90 degrees to the longitudinal axis of the recapture section 543. Preferably, the second plane of petals 512 is rotationally offset from the first plane of petals 510, such that the second petals 512 cover the spaces 514 formed between each adjacent pair of petals 510. The use of two or more layers of staggered petals 510 and 512 has been found to be useful in retrieving implants 100, particularly when the implant 100 carries a plurality of tissue anchors 118.

The recapture section 543, including the recapture section sheath portion 544, and the petals 510 and 512 may be manufactured from any of a variety of polymer materials useful in constructing medical device components such as the delivery catheter 302. This includes, for example, polyethylene, PET, PEEK, PEBAX, and others well known in the art. The second petals 512 may be constructed in any of a variety of ways. In one convenient construction, a section of tubing which concentrically fits over an implant release and recovery mechanism 200 delivery catheter 302 or the recapture section 543 is provided with a plurality of axially extending slots in the same manner as discussed above. The tubing with a slotted distal end may be concentrically positioned on the recapture section 543, and rotated such that the space between adjacent petals 512 is offset from the space between adjacent petals 510. The hub of the petals 512 may thereafter be bonded to the recapture section 543, such as by heat shrinking, adhesives, or other bonding techniques known in the art.

In the illustrated embodiment, the mesh sock 392 has a distal end which is coupled with the recapture section 543 and the sock 392 has a proximal end which is coupled with a sock attachment section 546. The flexible sock 392, such as a metallic mesh sock 392 (e.g., made from nickel titanium, or NITINOL) partially covers at least a portion of the outer surface of a catheter in an implant release and recapture mechanism 200. In FIG. 14B, the catheter is a deployment catheter 302. The mesh sock 392 is slideably received inside the transseptal catheter 520 or retrieval catheter 502. The mesh sock 392 can stretch longitudinally and can bend relative to the mesh sock's longitudinal axis, thereby allowing the recapture section 543 to adjust its axial inclination relative to the axis of the implant 100. The flexible sock 392 increases the flexibility of the system 50 and tends not to transmit moment arms and transmits compressive loads only after it has been sufficiently compressed.

Figure 15A:
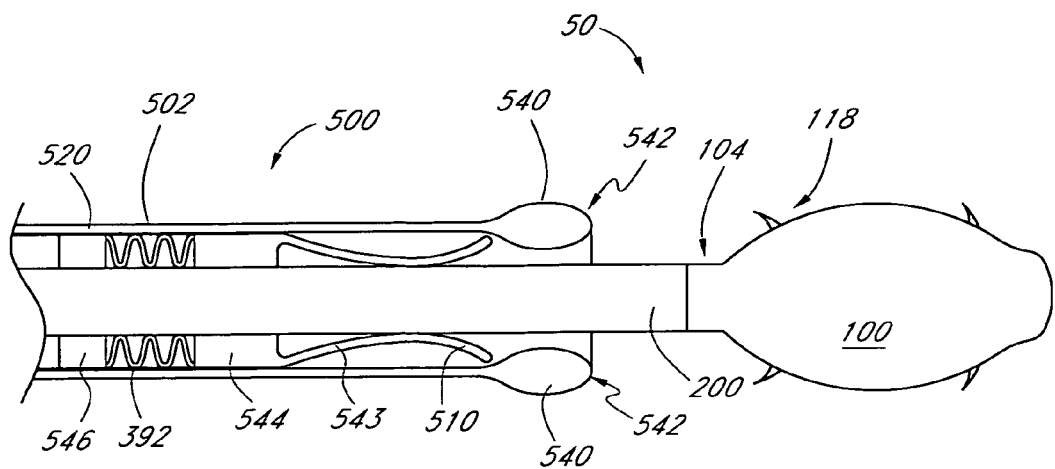
FIGS. 15A-15I illustrate a schematic cross sectional view of steps in a retrieval of an implant using a retrieval system with an extendible mesh sock and a transseptal sheath with an enlargeable portion at its distal end in accordance with an embodiment of the present invention.

In one embodiment the sock 392, which can be a braided, multi-stranded nickel titanium tube, is used to help achieve concentric application of tension to the implant 100 while holding the implant 100 in its radially-reduced configuration. In other embodiments the sock 392 may be used to retrieve an implant 100. Prototypes have shown tensile forces exceeding two times those used to collapse the implant 100; no bending resistance; and no compression load transfer over the first 50% of axial strain (e.g., the sock 392 flexibly collapses to a point, as illustrated in FIG. 15A). The sock 392 can provide tension forces through the recapture section 543 to the proximal end 104 of the implant 100.

The sock attachment section 546 may be any material which is attachable to a mesh sock 392 and an outer surface of a catheter in an implant release and recapture mechanism 200. In FIG. 14B, the catheter is a deployment catheter 302. In some embodiments, if the sock 392 is attachable to the catheter 302 directly, the sock attachment section 546 may be the portion of the sock 392 that is attached to the catheter 302. The sock attachment section 546 moves with respect to the catheter 302 and is not slideably engaged with the catheter 302 once it is connected to the catheter 302.

The sock 392 can be attached to the sock attachment section 546 and the recapture section 543 using any method known to those of skill in the art, including adhesive, welds, bonds, mechanical links, pins, etc. As illustrated in schematic views in FIGS. 14A through 15I, the sock 392 appears to abut the proximal face of the recapture section sheath portion 544 of the recapture section 543 and the distal face of the sock attachment section 546. In various embodiments, the sock 392 may actually be attached to the proximal face, distal face, an outer surface, an inner surface, or an integrated surface of a recapture section 543 or a sock attachment section 546.

In one embodiment, LOCTITE adhesive is used to bond the proximal end of the sock 392 to the proximal end of the recapture section 543. In other embodiments, the sock 392 is trapped with a laser weld or swaged ring, or the sock 392 may be re-flowed directly into the sock attachment section 546 or recapture section 543. In some embodiments, as described above, the sock 392 may be contiguous with the sock attachment section 546. The sock 392 can also be re-flowed directly into the catheter 302 outer lumen or it can be an extension of a braid that can be provided in the catheter 302.

The ability of the sock 392 to "spring back," or return to its initial state without taking a permanent set helps maintain consistent expansion and collapse properties during the implant 100 deployment and recapture processes. The superelastic properties of NITINOL are well-suited for use as the sock 392. In addition, a stainless steel braid will take a set and create compression bias as well. In various embodiments the sock 392 may be made of NITINOL, stainless steel, Elgiloy, titanium, or other elastic metals that are thermomechanically processed for high elasticity. Also, in some embodiments, sock 392 includes low section thickness components so that strains in the sock components, during sock use, are below the elastic limit of the sock material. In one embodiment, the sock 392 may use aspects of a puzzle lock profile (not illustrated here) as disclosed in co-pending U.S. application Ser. No. 11/607,253, filed Dec. 1, 2006, titled "METHOD AND APPARATUS FOR DELIVERING AN IMPLANT WITHOUT BIAS TO A LEFT ATRIAL APPENDAGE".

As illustrated in FIG. 14B, one embodiment of the implant release and recapture mechanism 200 includes an implant actuation shaft 334 and a catheter body 302. The catheter 302 can be any of the tubes being used in the system, including but not limited to a catheter delivery body 302 and a tubular body 306. As described above, the implant actuation shaft 334 may supply a distal force to the distal end of the implant 100 which may collapse the implant 100 into a radially-reduced configuration. The implant actuation shaft 334 may be any of the embodiments described herein. These components may work in conjunction with a pull wire 312 system as described above, or in a system where the implant actuation shaft 334 is a torque rod 340 or a rotatable core 342 as described above, or in other systems that may include a disconnect mount, a disconnect hub, flexible fingers, retractable locks, quick-connect interfaces, or quick-disconnect interfaces.

In one embodiment, the retrieval catheter system 500 includes a gripping portion 540 that when activated, engages, or grips the recapture section 543 at or near a recapture section sheath 544. Once the recapture section is engaged, the gripping portion is advanced distally with respect to the sock attachment section 546, as described in greater detail below. Distal advancement causes the sock 392 to stretch or extend distally, and allows the petals 510 of the recapture section 543 to be advanced out of the sheath 502 or 520. When the petals 510 are advanced, the implant 100 can be withdrawn into the petals 510 to protect the sheath 502 or 520 from the anchors 118 of the implant 100. Covering the anchors 118 with the petals 510 also helps facilitate recapturing the implant 100 within the sheath 502 or 520 so it may be removed from the patient's body.

Additional details regarding the recapture process are provided in greater detail below. In addition, details regarding the various embodiments of gripping portions suitable for use with a retrieval catheter system 500 are also described in greater detail below.

FIGS. 15A-15I illustrate an implant delivery system 50 with a retrieval catheter system 500 in accordance with one embodiment of the present invention. FIGS. 15A-15I illustrate steps in the recapture of an implant 100 into a retrieval catheter system 500 similar to the embodiments described in FIGS. 14A and 14B. The implant 100 has with a plurality of anchors 118 and is attached to an implant release and recapture mechanism 200. Illustrated in this embodiment is a transseptal sheath 520 which also acts as a retrieval catheter 502, an implant release and recapture mechanism 200, a mesh sock 392 attached to a sock attachment section 546 and a recapture section 543 with a plurality of petals 510 for facilitating proximal retraction of the implant 100. As described relating to FIGS. 14A and 14B, the implant release and recapture mechanism 200 in FIGS. 15 can be any embodiment of an implant release and recapture mechanism 200, including mechanisms using a deployment catheter 302 and an implant actuation shaft 334 as described relating to FIG. 14B.

Some embodiments of a retrieval catheter 502 (or transseptal sheath 520) include an enlargeable portion 540 (such as a gripping portion described above) and an a traumatic tip 542. In some embodiments the enlargeable portion 540 of the retrieval catheter 502 expands radially at the outer surface of the retrieval catheter 502 while it simultaneously reduces radially at the inner surface of the retrieval catheter 502. In other embodiments the enlargeable portion 540 may expand only radially outwardly. In other embodiments the enlargeable portion 540 may expand only radially inwardly, thereby decreasing the open lumen size defined by the inside of the retrieval catheter 502. In some embodiments, the enlargeable portion is a balloon. The enlargeable portion 540 of the retrieval catheter 502 may be located anywhere along the length of the catheter 502. In some embodiments the enlargeable portion 540 is located at a distal portion or a distal end of a retrieval catheter 502. The a traumatic tip 542 is designed to prevent injury to tissues within the body by using compliant, flexible materials and limiting sharp edges.

Figure 15B:
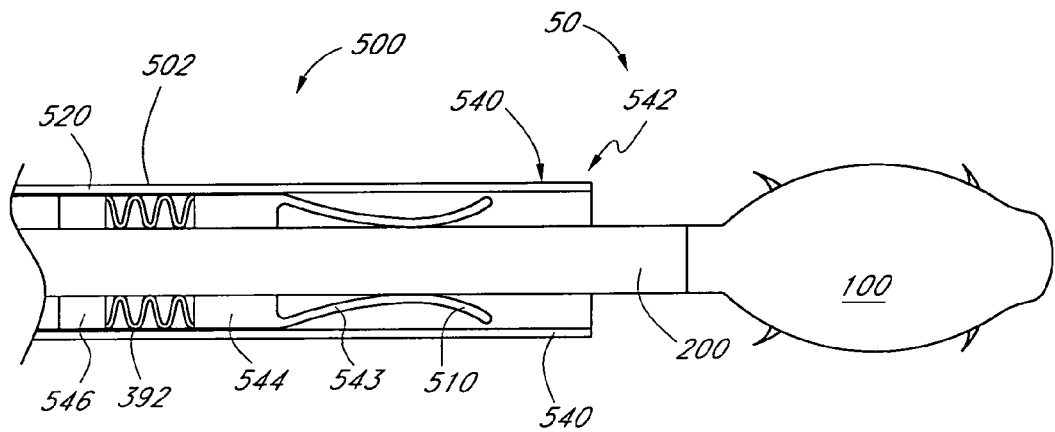

In the illustrated embodiments of FIGS. 15A-15I the retrieval catheter 502 is a transseptal sheath 520. In other embodiments, the retrieval catheter may be a separate catheter or another tube or catheter that is used in the implant deployment system 50. The enlargeable portion 540 can be adjusted from an enlarged inside diameter configuration (as shown in FIG. 15A), to a reduced inside diameter configuration (as shown in FIG. 15B) by any of a variety of mechanisms well known to those of skill in the art. For example, the enlargeable portion 540 can be inflated or filled with a fluid, such as saline or radiopaque contrast. These fluids may be controlled by injections into fluid ports in the handle 400 (not illustrated here) through channels (not illustrated here) in the retrieval catheter 502 that are in fluid communication with the injection ports. The enlargeable portion 540 of the retrieval catheter 502 may be selectively inflated to a reduced inside diameter configuration or deflated to an enlarged inside diameter configuration. The enlargeable portion 540 may be inflated to varying degrees to completely close off the end retrieval catheter 502 when all coaxial components are withdrawn proximal to the enlargeable portion 540. The enlargeable portion 540 may be inflated to grasp the implant actuation shaft 334, the recapture section 543, the mesh sock 392, or the catheter body 302.

A sequence of steps in accordance with one embodiment of the present invention for the retrieval and removal of an implant 100 from the LAA 10 using a retrieval catheter system 500 on an implant delivery system 50 is depicted in FIGS. 15A-15I. As mentioned above, FIGS. 15A-15I illustrate the recapture of an implant 100 with a plurality of anchors 118 into a retrieval catheter system 500 subsequent to the radial-reduction of the implant 100 within the LAA 10, as described above and relating to FIGS. 14A-14B.

In FIG. 15A, the implant release and recapture mechanism 200 is engaged with the implant 100. The sock 392 is compressed proximally in order to stow the petals 510 of the recapture section 543 within the transseptal sheath 520. The implant 100 may be in a radially-expanded, radially-reduced, or intermediate configuration. Prior to recapture, the implant 100 may be removed or withdrawn from the LAA 10 (not shown). As illustrated, the implant 100 is in a partially radially-reduced configuration detached from the LAA 10. The enlargeable portion 540 of the retrieval catheter 502 may be in its inflated state to work with the a traumatic tip 542 to reduce incidental trauma to surrounding tissue as the retrieval catheter 502 is advanced distally toward the implant 100. Alternatively, the enlargeable portion 540 may be in its deflated state, as illustrated in FIG. 15B.

In FIG. 15B, the enlargeable portion 540 of the retrieval catheter 502 is deflated in order to allow other components proximal to the retrieval catheter 502 to emerge distally out of the transseptal sheath 520.

Figure 15C:
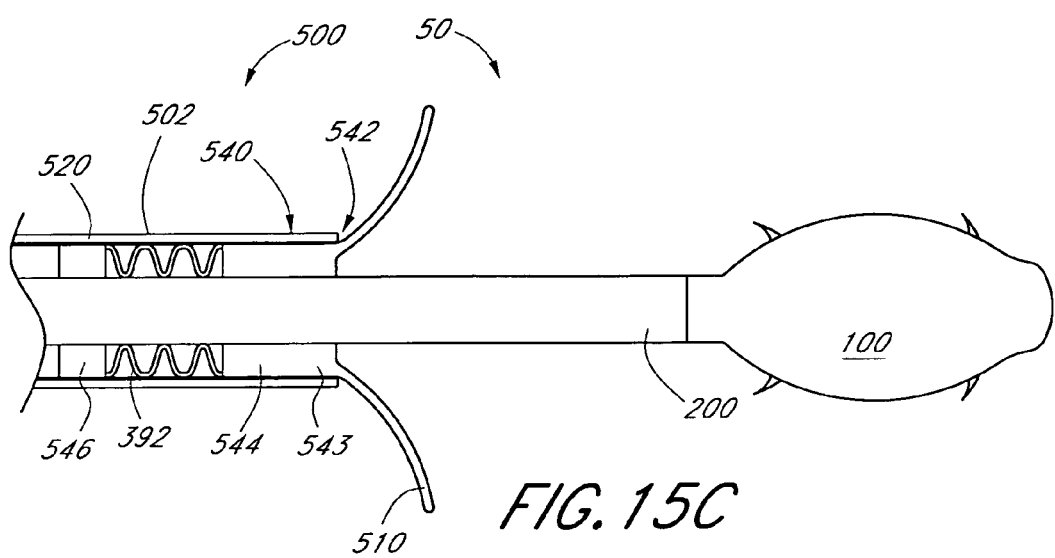

In FIG. 15C, the retrieval catheter 502 is withdrawn proximally with respect to the implant release and recapture mechanism 200 in order to allow the petals 510 of the recapture section 543 to expand radially. In one embodiment this distance is about 5 cm. Alternatively, a similar effect would result from keeping the retrieval catheter 502 stationary while distally advancing the implant release and recapture mechanism 200 along with the sock attachment section 546 and the implant 100 distally into the heart 5 (not pictured), which would compress the mesh sock 392 and distally advance the recapture section 543 so that the petals 510 would radially expand distal to the end of the recapture catheter 502.

Figure 15D:
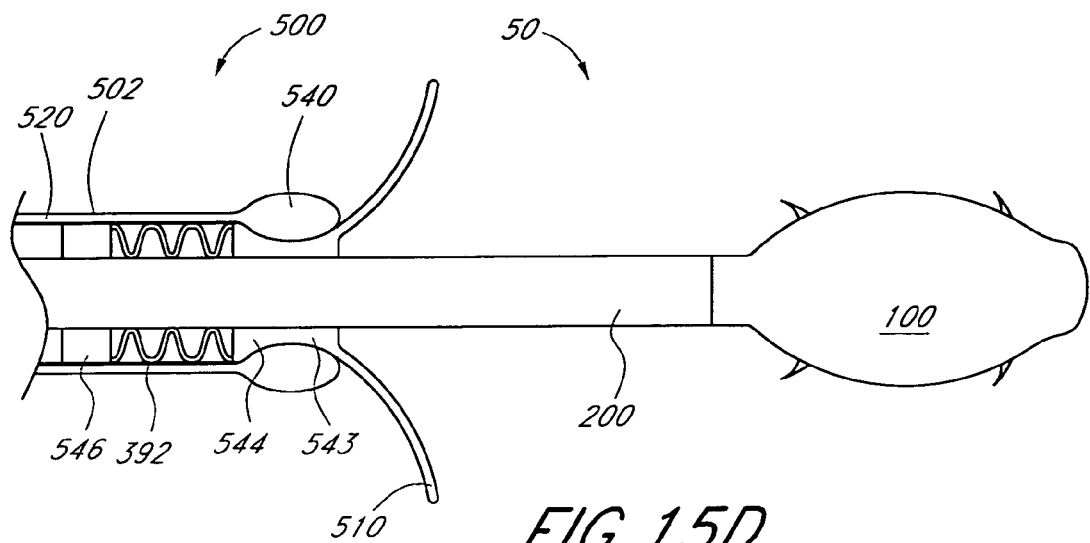

In FIG. 15D, the enlargeable portion 540 of the retrieval catheter 502 is inflated to grasp the recapture section 543. Alternatively, the retrieval catheter 502 could be inflated to grasp a distal portion of the sock 392 in order to distally advance the recapture section 543. Advancement of the flexible sock 392 would stretch the sock 392 from a relatively fixed point at the sock attachment section 546, sliding the recapture section 543 distally as shown in FIG. 15E.

Figure 15E:
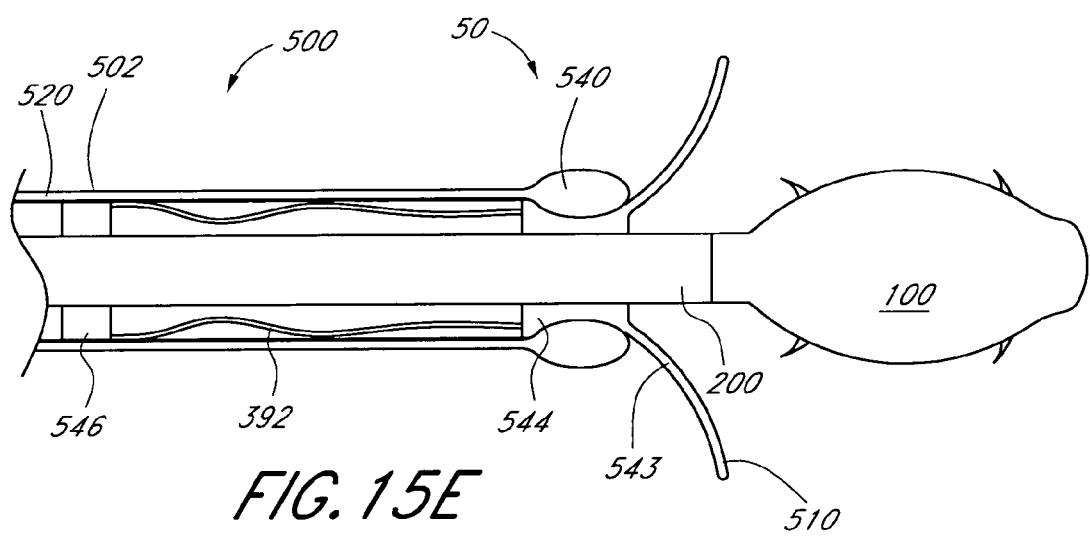
Figure 15F:
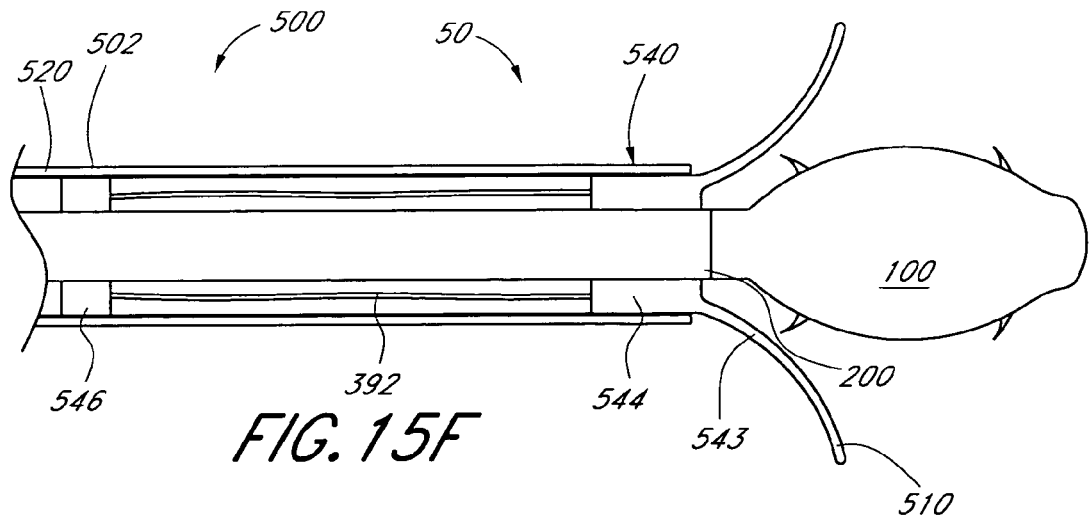

In FIG. 15E, the enlargeable portion 540 remains inflated to grasp and move the recapture section 543 to a proximal end 104 of the implant 100 such that the petals 510 substantially surround the collapsed implant 100 and are properly aligned to recapture the implant 100. In FIG. 15F, the enlargeable portion 540 is deflated to allow the implant release and recapture mechanism 200, flares 510, and implant 100 to move proximally with respect to the recapture sheath 502.

Figure 15G:
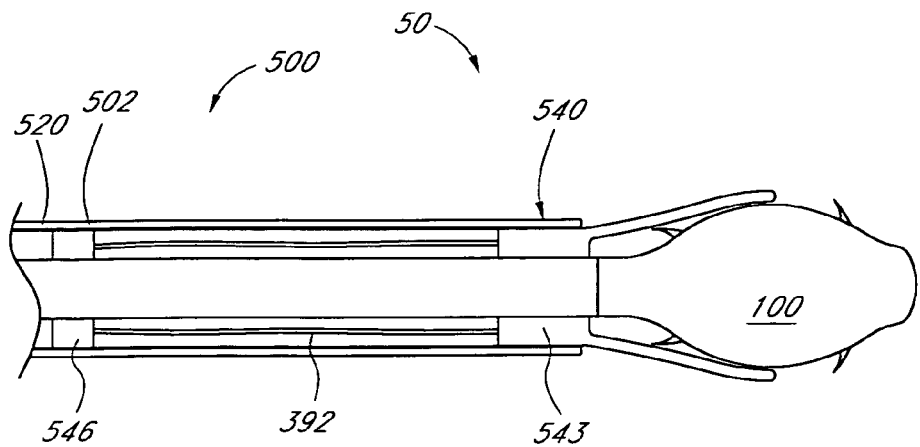

In FIG. 15G, the implant release and recapture mechanism 200, flares 510, and implant 100 move proximally with respect to the recapture sheath 502. As the flares 510 enter the recapture transseptal sheath 502, the flares 510 bend to cover the barbs 118 on the implant 100 which is further radially reduced as it enters the recapture catheter 502. As the implant release and recapture mechanism 200 moves proximally, it moves the sock attachment section 546 with it since both are attached to each other.

Figure 15H:
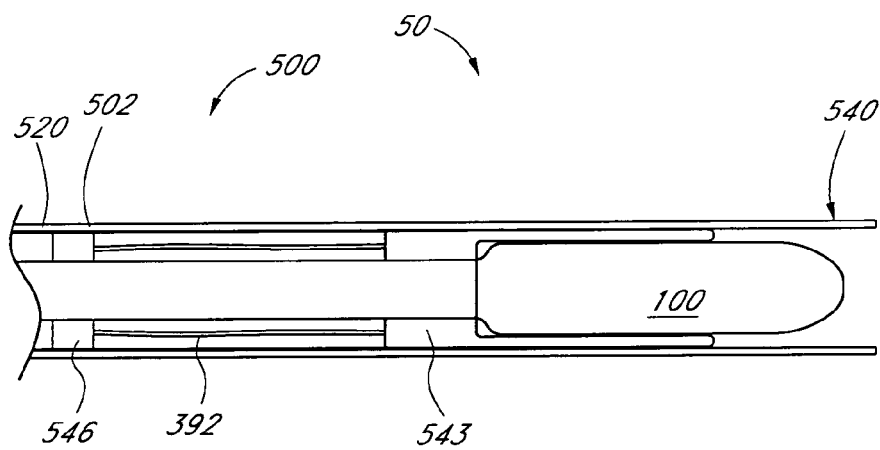
Figure 15I:
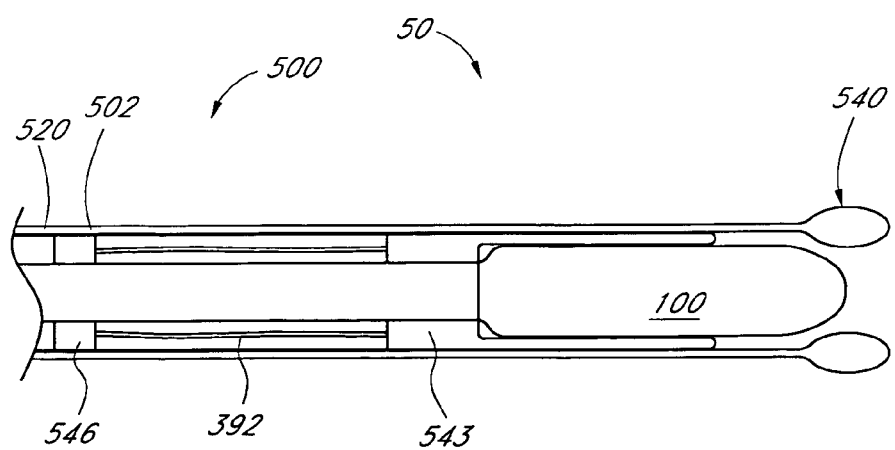

In FIG. 15H the implant 100 is withdrawn proximally so that it is recaptured inside the recapture catheter 502. In FIG. 15I the enlargeable portion 540 may be optionally inflated to lock the implant 100 inside the recapture catheter or to work with the a traumatic tip 542 to shield the body from damage from the end of the catheter 502. The entire assembly can then be withdrawn from the patient's vasculature.

FIGS. 16-18 illustrate an implant delivery system 50 having a retrieval catheter system 500 in accordance with another embodiment of the present invention. The embodiments illustrated in FIGS. 16-18 are similar in many ways to the embodiments illustrated in Figures 15A-15E but instead of using an enlargeable portion 540 of a transseptal sheath 520, the embodiments in FIGS. 16-18 use a cam 550 actuated by at least one pull wire 548 in a multi-lumen shaft 326. As with the embodiments in FIGS. 15A-15E, the retrieval catheter system 500 attaches near the distal end of an implant release and recapture mechanism 200.

The integral recapture section allows the recapture mechanism to be invisible to user until needed thus eliminating the extra preparation and manipulation steps of a delivery system 50 having a separate recapture shaft 502 such as described above. These embodiments of the retrieval catheter system 500 may be used in conjunction with any of the embodiments of an implant release and recapture mechanism 200 disclosed herein or in other patents and applications incorporated by reference.

During retrieval, certain embodiments of the implant release and recapture mechanism 200 engage the implant 100 in order to radially-reduce the implant 100, as described above. Once the implant 100 is reduced to its radially-reduced configuration within the LAA 10, the system 50 with the implant 100 attached can be withdrawn proximally out of the LAA 10. In order to complete the recapture of the implant 100, the implant 100 can be withdrawn in to the retrieval catheter system 500 in order to prevent damage to the heart and the rest of the body by an exposed implant.

In FIGS. 16-18, embodiments of the retrieval catheter system 500 may be used in conjunction with an implant release and recapture mechanism 200 and an implant 100 located within a LAA. One embodiment of a retrieval catheter system 500 uses a cam 550 actuated by at least a pull wire 548 in a multi-lumen shaft 326.

The multi-lumen shaft 326 is described in more detail below. In this embodiment, the multi-lumen shaft 326 may comprise a five-lumen shaft as illustrated in FIG. 19A. The multi-lumen shaft 326 comprises a core lumen 328 for holding an implant actuation shaft 334, at least one control line lumen 330 and at least one proximal injection lumen 332 in communication with proximal injection port 412.

Figure 16A:
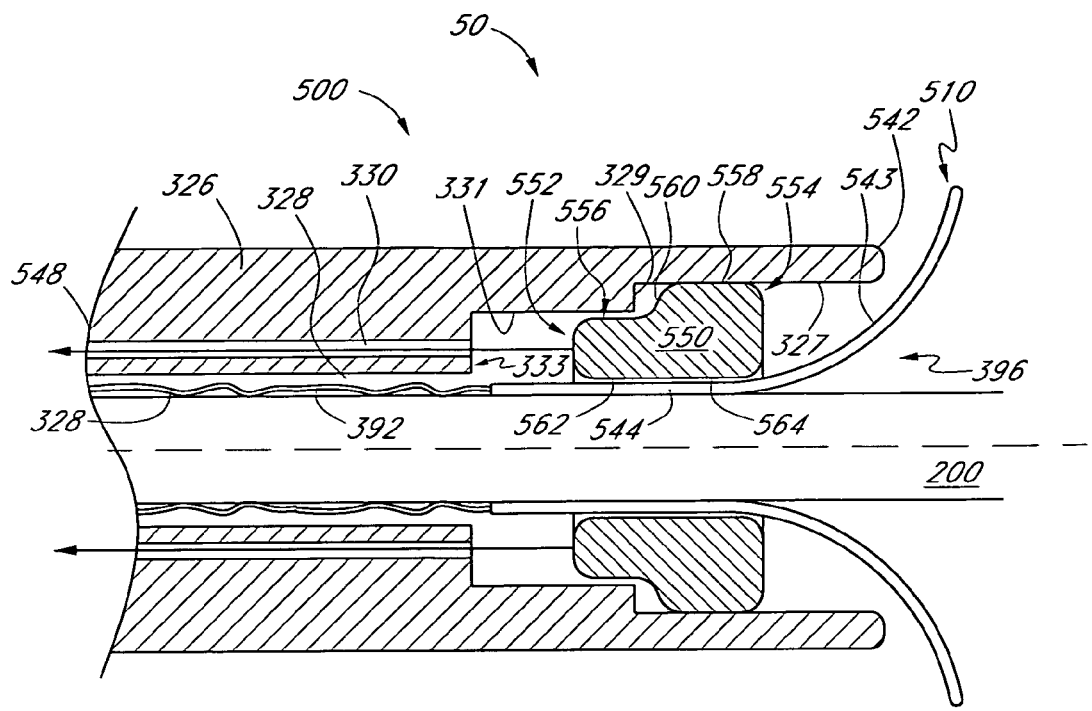
FIG. 16A illustrates a schematic cross sectional view of a retrieval system with a cam in a non-compressed state and a pull wire housed in a multi-lumen sheath in accordance with an embodiment of the present invention.
Figure 16B:
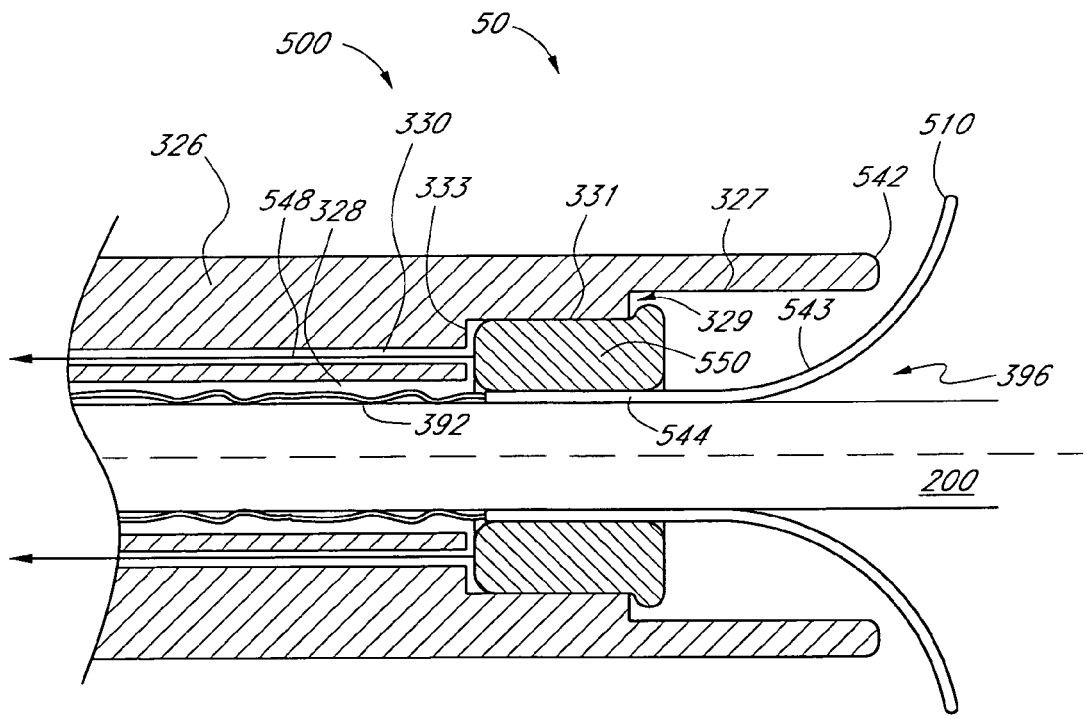
FIG. 16B is a cross sectional schematic view as in FIG. 16A of the retrieval system with the cam actuated in a compressed state.

As illustrated in FIG. 16A-16B, the multi-lumen shaft 326 comprises a main distal lumen 396, a first lumen surface 327, a second lumen surface 329, a third lumen surface 331, and a fourth lumen surface 333. In this embodiment, the main distal lumen 396 is a single lumen at the distal end of the multi-lumen shaft 326 which starts at the distal termination point of the multiple lumens 328, 330 and 332 and continues to the distal tip of the multi-lumen shaft 326. The first lumen surface 327 starts at the distal interior surface of the main lumen 396 of the multi-lumen shaft 326 just proximal to an a traumatic tip 542.

The first lumen surface 327 runs parallel to the longitudinal axis of the multi-lumen shaft 326. The a second lumen surface 329 is proximal to and abuts the first lumen surface 327 and acts as a transition to a radially reduced portion of the main lumen 396 of the multi-lumen shaft 326. The second lumen surface 329 can be perpendicular to the first lumen surface 327, or in some embodiments the second lumen surface 329 may act as a ramp transition to the radially reduced portion of the main lumen 396 of the multi-lumen shaft 326. The third lumen surface 331 is proximal to and abuts the second lumen surface 329, and is a radially reduced portion of the main 396 lumen of the multi-lumen shaft 326. The third lumen surface 331 runs parallel to the longitudinal axis of the multi-lumen shaft 326. The fourth lumen surface 333 defines the proximal surface of the main lumen 396 of the multi-lumen shaft 326.

The cam 550 has a proximal surface 552, a distal surface 554, a proximal outer surface 554, a distal outer surface 558, an outer transition surface 560, a proximal inner lumen surface 462, and a distal inner lumen surface 564. The cam 550 is made of an elastic, radially compressible material or structure. In one embodiment, the cam 550 is a multi-level ring-like structure, as described herein. At least one pull wire 548 is attached to the proximal surface 552 of the cam 550, and runs through a control-line lumen 330 in the multi-lumen shaft 326 to a control knob in a handle 400, as described below. The proximal outer surface 554 is configured to fit in a portion of the main lumen 396 corresponding to the third lumen surface 331. The distal outer surface 558 is configured to fit in a portion of the main lumen 396 corresponding to the first lumen surface 327 in a non-compressed state. In some embodiments, the proximal outer surface 554 has a radius that is less than the radius of the distal outer surface 558. The outer transition surface 560 is designed to interact with the second lumen surface 329 to compress the distal outer surface 558 into the third lumen surface 331 when sufficient proximally directed force is applied to the pull wire 548. The proximal inner lumen surface 462 and the distal inner lumen surface 564 are sized and configured to receive a recapture section 543 and an implant release and recapture mechanism 200.

Also illustrated is a recapture section 543 with a recapture section sheath 544 and flares 510 attached to a mesh sock 392, both slidably engaged with the outer surface of an implant recapture and release mechanism 200, such as a catheter body 302, as discussed above. When the cam 550 is aligned with the recapture section sheath 544 on the recapture section 543, at least one pull wire 548 can be pulled distally to pull the proximal surface 552 of the elastic cam 550 in a distal direction, forcing the larger diameter of the distal outer surface 558 into the smaller diameter third lumen surface 331 lumen. Since the cam 550 is elastic, the cam 550 will fit in the smaller space while applying inwardly radially directed force on the recapture section sheath 544 on the recapture section 543. This engagement will allow the axial sliding of the multi-lumen shaft 326 to control the slideable motion of the recapture section 543 with respect to the implant recapture and release mechanism 200, such as a catheter body 302. While the multi-lumen shaft 326 is moved distally with respect to the implant recapture and release mechanism 200, the fourth lumen surface 333 may abut the proximal surface 552 of the cam 550 to prevent any binding of the cam 550 within the core lumen 328. While the multi-lumen shaft 326 is moved distally with respect to the implant recapture and release mechanism 200 the sock 392 will expand allowing the recapture section 543 to slide distally toward an implant 100 (not illustrated here).

Figure 17A:
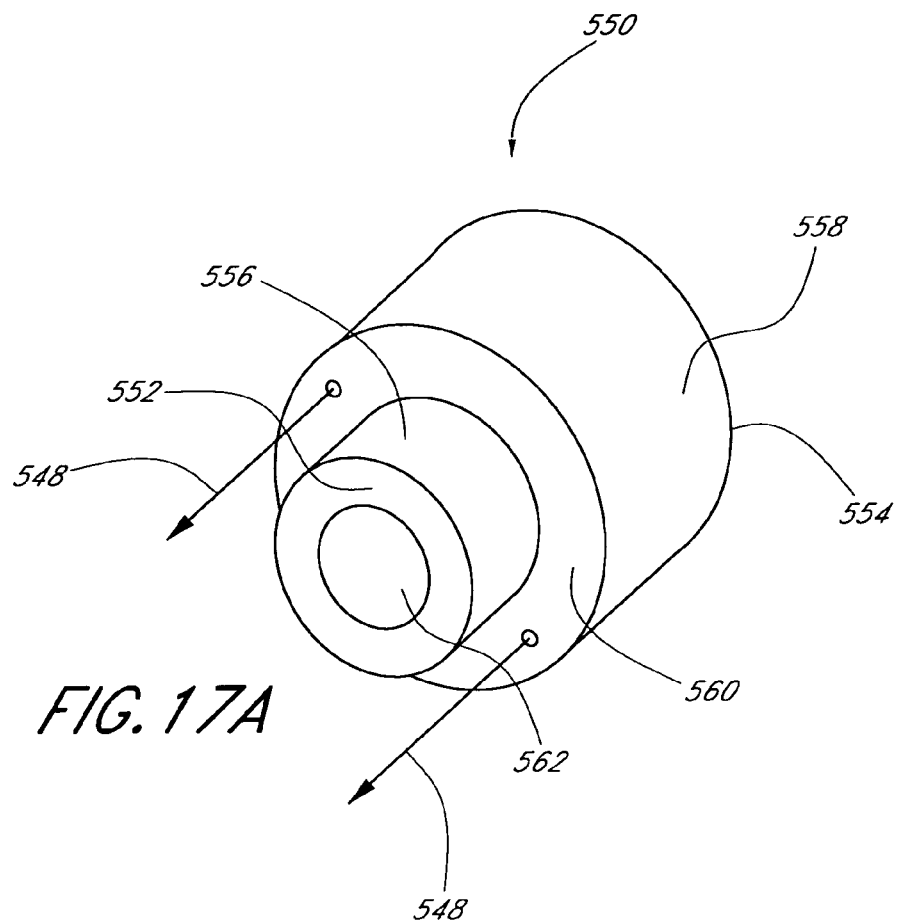
FIG. 17A illustrates a perspective view of a cam in a non-compressed state with two pull wires in accordance with an embodiment of the present invention.
Figure 17B:
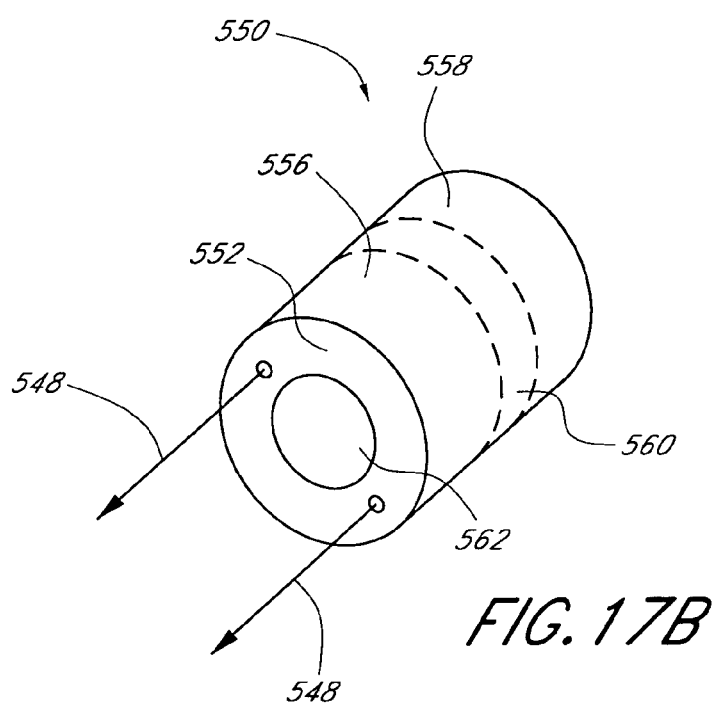
FIG. 17B is a perspective view as in FIG. 17A of the cam actuated in a compressed state.

As illustrated in FIGS. 17A-17B, one embodiment of an elastic cam 550 with pull-wires 548 is shown in a non-compressed state (FIG. 17A) within a main distal lumen 396 (not illustrated) of a multi-lumen shaft 326 (not illustrated) and then in a compressed state (FIG. 17B) within a main distal lumen 396 (not illustrated) of a multi-lumen shaft 326 (not illustrated). In some embodiments, the proximal outer surface 554 has a radius that is less than the radius of the distal outer surface 558 in a non-compressed state. In other embodiments, the proximal outer surface 554 has a radius that is substantially the same as the radius of the distal outer surface 558 in a non-compressed state, where the radius corresponds to the radius of the first lumen surface 327 of the main lumen 396 of the multi-lumen shaft 326. In this type of embodiment, the entire cam 550 sits primarily in the lumen defined by the first lumen surface 327 in a non-compressed state before being compressed into the lumen defined by the third lumen surface 331. In the compressed state, the proximal outer surface 554, distal outer surface 558, and outer transition surface 560 are substantially the same radius corresponding to the third lumen surface 331.

Referring to FIGS. 18A-18H, there is illustrated an implant delivery system 50 with a retrieval catheter system 500 in accordance with one embodiment of the present invention. FIGS. 18A-18H illustrate steps in the recapture of an implant 100 into a retrieval catheter system 500 using the embodiments described in FIGS. 16A, 16B, 17A, and 17B. The retrieval catheter system 500 of this embodiment is a multi-lumen shaft 326. The implant 100 has with a plurality of anchors 118 and is attached to an implant release and recapture mechanism 200.

Figure 18A:
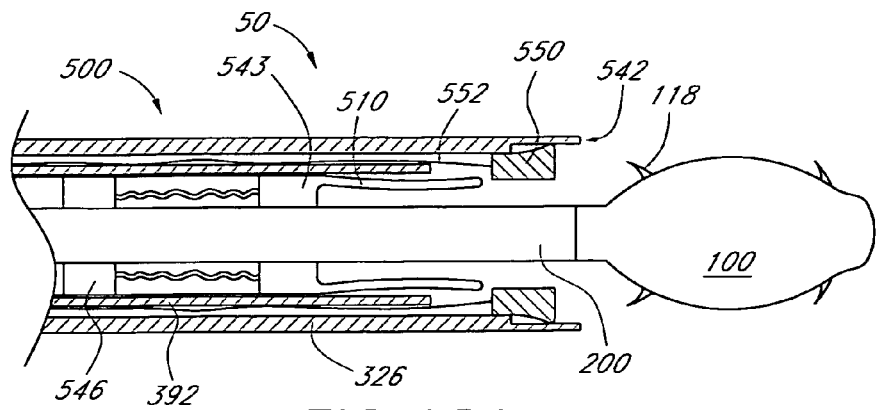
FIGS. 18A-18H illustrates a schematic cross sectional view of steps in a retrieval of an implant using a retrieval system with an extendible mesh sock and a multi-lumen sheath and a cam in accordance with an embodiment of the present invention.

In FIG. 18A, the implant release and recapture mechanism 200 is engaged with the implant 100. The sock 392 is compressed proximally in order to stow the petals or flares 510 of the recapture section 543 within a core lumen 328 of a multi-lumen shaft 326. The implant 100 may be in a radially-expanded, radially-reduced, or intermediate configuration. Prior to recapture, the implant 100 is removed from the LAA 10 (not shown). As illustrated, the implant 100 is in a partially radially-reduced configuration detached from the LAA 10. The cam 550 is in its non-compressed state with the distal outer surface 558 of the cam 550 in the lumen defined by the first lumen surface 327 of the multi-lumen shaft 326.

Figure 18B:
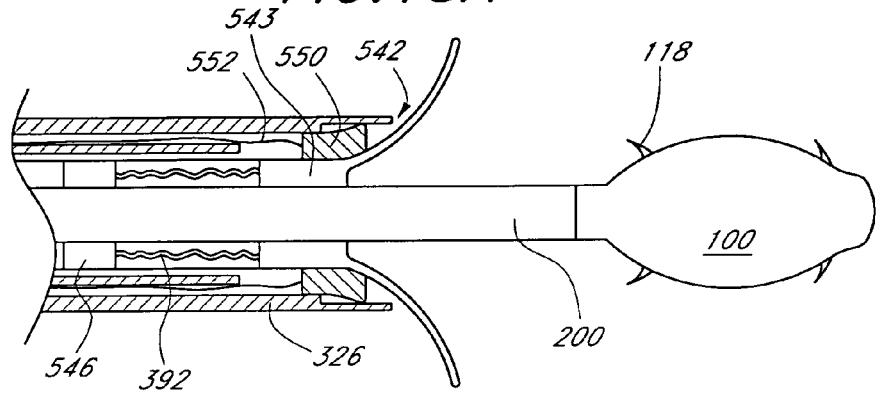

In FIG. 18B, the multi-lumen shaft 326 is withdrawn proximally with respect to the implant release and recapture mechanism 200 in order to allow the petals 510 of the recapture section 543 to expand radially. In one embodiment this distance is about 5 cm. Alternatively, a similar effect would result from keeping the multi-lumen shaft 326 stationary while distally advancing the implant release and recapture mechanism 200 along with the sock attachment section 546 and the implant 100 distally into the heart 5 (not pictured), which would compress the mesh sock 392 and distally advance the recapture section 543 so that the petals 510 would radially expand distal to the end of the multi-lumen shaft 326.

Figure 18C:
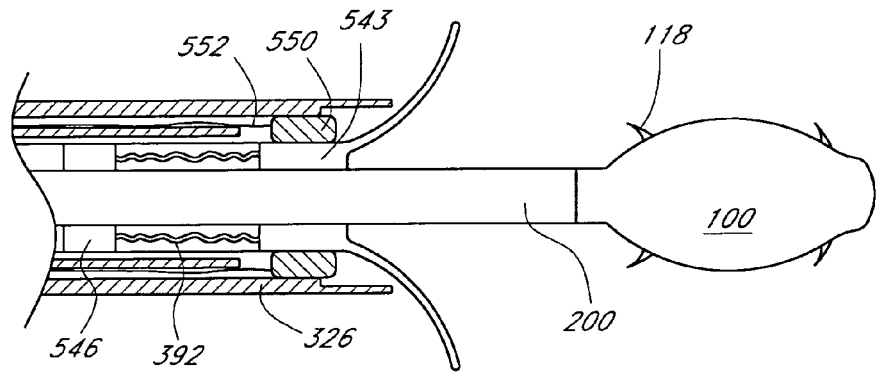

In FIG. 18C, the pull-wires 552 are pulled proximally to actuate the elastic cam 550 into a compressed state to engage a recapture section sheath 544 of a recapture section 543, as described above. Alternatively, the cam 550 could to grasp a distal portion of the sock 392 in order to distally advance the recapture section 543. Advancement of the flexible sock 392 would stretch the sock 392 from a relatively fixed point at the sock attachment section 546, sliding the recapture section 543 distally as shown in FIG. 18D.

Figure 18D:
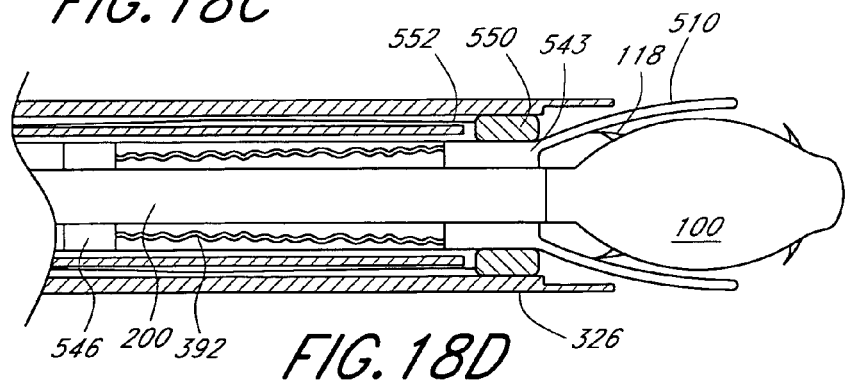

In FIG. 18D, the cam 500 remains in its compressed state to grasp and move the recapture section 543 to a proximal end 104 of the implant 100 such that the petals 510 substantially surround the collapsed implant 100 and are properly aligned to recapture the implant 100.

Figure 18E:
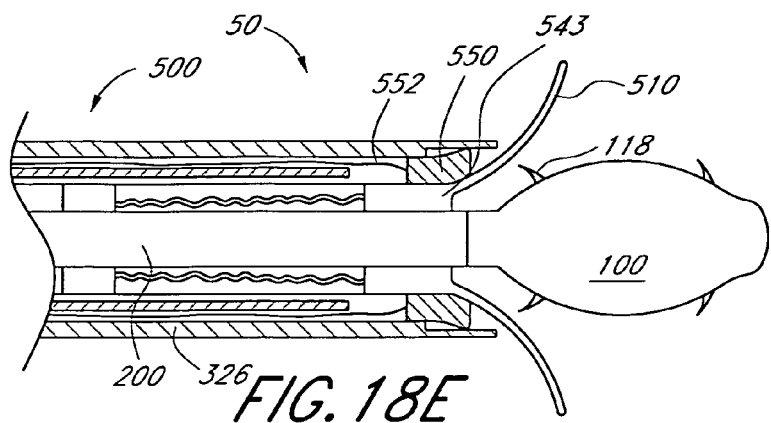

In FIG. 18E, the tension in the pull wires 548 is released to allow the cam 550 to revert to its non-compressed state. In some embodiments, the elasticity of the cam 550 will bias the cam 550 to return to its non-compressed state once the tension in the pull wires 548 is released. In some embodiments, the multi-lumen shaft 326 can be retracted proximally with respect to the implant release and recapture mechanism 200 in order for the cam 550 to return to its non-compressed state. Once the cam 550 is in its non-compressed state the flares 510 and implant 100 can move proximally with respect to the multi-lumen shaft 326.

Figure 18F:
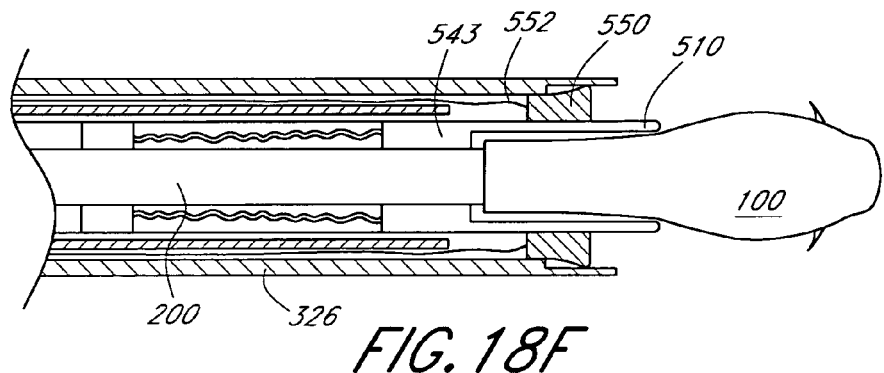

In FIG. 18F, the implant release and recapture mechanism 200, flares 510, and implant 100 move proximally with respect to the multi-lumen shaft 326. As the flares 510 enter the core lumen 328 of the multi-lumen shaft 326, the flares 510 bend to cover the barbs 118 on the implant 100 which is further radially reduced as it enters the core lumen 328 of the multi-lumen shaft 326. As the implant release and recapture mechanism 200 moves proximally, it moves the sock attachment section 546 with it since both are attached to each other.

Figure 18G:
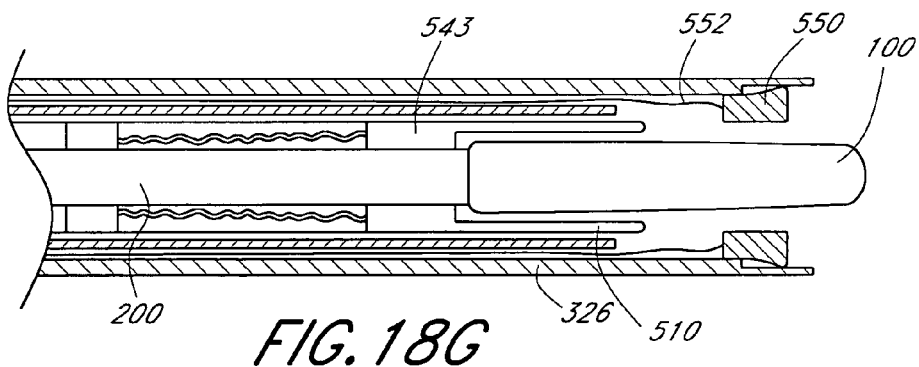
Figure 18H:
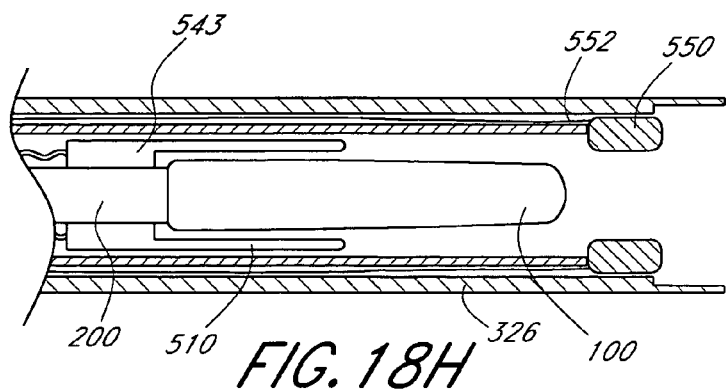

In FIG. 18G the implant 100 is substantially recaptured inside the multi-lumen shaft 326. In FIG. 18H the cam 550 may be optionally be actuated into its compressed state in order to lock the implant 100 inside the multi-lumen shaft 326.

3. Deployment Catheter and Deployment Handle

Referring again to FIG. 2, there is illustrated a block diagram representing an implant delivery system 50 suitable for use with any and all of the embodiments discussed herein. The implant delivery system 50 includes an implant 100, an implant release and recapture mechanism 200, a catheter system 300 and a deployment handle 400. FIG. 2A illustrates one embodiment of an implant delivery system 50 comprising particular examples of an implant 100, an implant release and recapture mechanism 200, a catheter system 300 and a deployment handle 400.

Referring again to FIG. 11, there is schematically illustrated a further embodiment of the present invention. An adjustable implant delivery system 50 comprises generally a catheter 302 for placing a detachable implant 100 within a body cavity or lumen, as has been discussed. The catheter 302 comprises an elongate flexible tubular body 306, extending between a proximal end 308 and a distal end 310. The catheter is shown in highly schematic form, for the purpose of illustrating the functional aspects thereof. The catheter body will have a sufficient length and diameter to permit percutaneous entry into the vascular system, and transluminal advancement through the vascular system to the desired deployment site. For example, in an embodiment intended for access at the femoral vein and deployment within the left atrial appendage, the catheter 302 will have a length within the range of from about 50 cm to about 150 cm, and a diameter of generally no more than about 15 French. Further dimensions and physical characteristics of catheters for navigation to particular sites within the body are well understood in the art and will not be further described herein.

The tubular body 306 is further provided with a handle 402 generally on the proximal end 308 of the catheter 302. The handle 402 permits manipulation of the various aspects of the implant delivery system 50, as will be discussed below. Handle 402 may be manufactured in any of a variety of ways, typically by injection molding or otherwise forming a hand-piece for single-hand operation, using materials and construction techniques well known in the medical device arts.

FIG. 19 (which is similar to FIG. 2A) illustrates one embodiment of an implant delivery system 50 comprising an operably connected implant 100, an implant release and recapture mechanism 200, a catheter system 300 and a deployment handle 400. As shown in FIG. 22, the embodied catheter system 300 comprises a peel-away sheath 314, a recapture sheath 522, a deployment catheter 302, a loading collar 323, a multi-lumen shaft 326, and an axially moveable core 304, each described further below. The system 50 may also include a transseptal sheath 520 (not illustrated here) that is substantially coaxial and external to the other catheters. In some embodiments, the transseptal sheath may be one of the other catheters. The deployment handle 400 comprises a handle 402, a control knob 408, a release knob 410, a proximal injection port 412 and a distal injection port 414. Injection ports 546, 548, as shown in FIG. 22, preferably are provided in the delivery system 50 to allow contrast injection proximally and distally of the implant 100 to facilitate in-vivo assessment of the positioning and seal quality of the implant 100.

Referring again to FIG. 19, illustrated is an embodiment of an implant delivery system 50. When an embodiment of the delivery system 50 is assembled, a recapture sheath 522 is loaded over the deployment catheter 302, distal to the handle 402. The recapture sheath 522 is designed to allow recapture of the implant 100 prior to its final release, such as described with respect to retrieval catheter 502 above. Recapture petals or flares 510 may be provided on the distal end 506 of the recapture sheath 522 to cover the anchors 118 of the implant 100 during retrieval into the transseptal sheath 520, as described above with respect to FIGS. 13C-13E, and further below. A Touhy-Borst adapter or valve 530 may be attached to the proximal end 524 of the recapture sheath 522. The recapture sheath 522 comprises a radiopaque marker 528 on its distal end 526 near the recapture flares 510. The recapture sheath 522 comprises a recapture sheath injection port 529 for delivering fluid proximal the implant 100.

An embodiment of the peel-away sheath 314 is provided over a portion of the recapture sheath 522, between Touhy-Borst valve 530 and recapture flares 510. The peel-away sheath 314 is used to introduce a catheter 302 into a transseptal sheath 520 (not illustrated). As shown in FIG. 19, an embodiment of the peel-away sheath 314 comprises a locking collar 315, a peel-away section 316, and a reinforced section 317. The locking collar can be unlocked relative to peel-away section 316, and may include a threaded hub 318 that releasably engages tabs 319 of the peel-away section 316.

An embodiment of the loading collar 323 is located over a portion of the peel-away sheath 314 and a portion of the recapture sheath 522 with its proximal end being located over the peel-away sheath 314 at its distal end loaded over recapture sheath 522. The loading collar 323 can accommodate loading a collapsed implant 100 into the peel-away sheath 314 as described below. An embodiment of the loading collar 323 comprises a first end portion 324 adapted to receive and extend over a collapsed implant 100, and a second end portion 325 configured to guide the collapsed implant 100 into the peel-away sheath 314. The loading collar 323 may be made of stainless steel.

In order to assemble an embodiment of the delivery system 50, the axially movable core 304 and control line 312 are fed into the multi-lumen shaft 326 of the deployment catheter 302. The multi-lumen shaft 326 is then coupled with components of the deployment handle 400 and the injection port components 412, 414. The peel-away sheath 314 and the loading collar 323 are slid onto the recapture sheath 522, and the recapture sheath 522 is slid onto the deployment catheter 302. The implant 100 is then loaded on an end of the axially movable core 304 and coupled with the control line 312.

In an embodiment of the deployment catheter system 300, a catheter 302 is used in connection with a transseptal sheath 520 (not illustrated) to advance the implant 100 for deployment in a patient. The transseptal sheath 520 is a tubular device that in one embodiment can be advanced over a guidewire (not shown) for accessing the LAA 10 of a patient's heart 5. Transseptal sheath 520 in one embodiment has a permanent bend. A hemostasis valve (not illustrated) is provided at the proximal end of transseptal sheath. A fluid injection port is also provided at the proximal end to delivery fluid such as contrast media through the transseptal sheath. Systems and methods for implanting the device 100 in the LAA 10 are described further below.

In one embodiment, the multi-lumen shaft 326 comprises a five-lumen shaft as illustrated in FIG. 19A. The multi-lumen shaft 326 comprises a core lumen 328 for holding an implant actuation shaft 334, at least one control line lumen 330 and at least one proximal injection lumen 332 in communication with proximal injection port 412.

An axially moveable core 304 preferably extends from the deployment handle 400 through the core lumen 328 of the catheter 302 and couples the implant 100 of the delivery system 50. A control line 312 (referred to previously as a pull wire 312) preferably extends through the control line lumen 330 and preferably couples a proximal hub 104 of the implant 100 to the deployment handle control knob 408, allowing for implant 100 expansion and collapse. The control line 312 preferably extends around a portion of the axially movable core 304 near the proximal hub 104 of the implant 100, and is coupled to the implant 100 by crosspin 146, as described above.

B. Configurations and Methods of Use of an Implant Delivery System

Referring to FIG. 6, illustrated is an embodiment of an implant delivery system 50. The system and method allows for access and assessment of the LAA 10. In one embodiment, a guidewire (not shown) is used to access the superior vena cava through groin access. A transseptal sheath 520 is advanced over the guidewire and into the superior vena cava. The guidewire is removed and replaced with a transseptal needle (not shown). The transseptal sheath 520 preferably is retracted inferiorly so that a bend in the transseptal sheath directs the distal tip of the transseptal sheath toward the fossa ovalis. The needle is advanced to puncture the fossa ovalis. The transseptal sheath 520 is advanced to establish access to the LAA 10 and the needle is retracted. Further details or disclosure are provided above and in copending U.S. patent application Ser. No. 09/435,562 and U.S. pat. No. 7,044,134, issued May 16, 2006, the entireties of which are hereby incorporated by reference.

After preparing a transseptal sheath 520 for LAA 10 access, the size of the neck diameter and morphology of the LAA 10 preferably is determined by advancing the transseptal sheath 520 to the distal portion of the LAA 10 and injecting contrast media to obtain an initial left atrial appendogram. The neck diameter preferably is measured approximately 5 mm in from the ostium of the LAA 10 at end diastole.

Referring to FIG. 19, illustrated is an embodiment of a system and method that allows for selection and preparation of a deployment system 50. A deployment system 50 preferably comprises an implant 100 of an appropriate size for placement in a patient. Initially, the implant 100 preferably is in an expanded configuration, with axially moveable core 304 engaging the implant 100, as described above. The recapture sheath 522 preferably is positioned so it covers and supports the flexible segment 384 of the delivery system 50, wherein the flexible catheter section 362 of deployment catheter 302 and flexible core section 372 of axially moveable core 304 are aligned. The Touhy-Borst valve 530 preferably is tightened over the deployment catheter 302 to prevent relative movement between recapture sheath 522 and deployment catheter 302. The loading collar 323 and peel-away sheath 314 preferably are positioned so they are at the base of the recapture flares 510, proximal thereto.

In one embodiment, the delivery system 50 is loaded by rotating the control knob 408 counterclockwise until the implant 100 is fully collapsed. Preferably, at least a portion of the control line 312 is coupled with the control knob 408 such that rotation of the control knob 408 retracts at least a portion of the control line 312. In an embodiment, the rotation of the control knob 408 is in the counterclockwise direction to retract at least a portion of the control line 312. Retraction of the control line 312 preferably places tension on the proximal hub 104 of the implant 100, because a portion of the control line 312 preferably is coupled with the proximal hub 104 by a pin 146. While the distal portion of the axially moveable core 304 applies a distal force to distal hub 108 of the implant 100, tension in the control line 312 preferably causes the proximal hub 104 of the implant 100 to move proximally relative the axially moveable core 304, thereby collapsing the implant 100.

The diameter of the implant 100 preferably is reduced to approximately $\frac{1}{3}^{rd}$ or less of its original diameter when collapsed. The loading collar 323 and peel-away sheath 314 are then advanced distally over the flares 510 and implant 100 until the distal tip of the implant 100 is aligned with the distal end of the peel-away sheath 314 and the distal end of the loading collar is about 1.5 cm from the distal tip of the implant 100. At this point, the flares 510 partially cover the implant. The loading collar 323 preferably is removed and discarded.

With the implant 100 partially within the recapture sheath 522 and retracted within the peel-away sheath 314, the entire system preferably is flushed with sterile heparinized saline after attaching stopcocks to the recapture sheath injection port 529, the proximal injection port 412 and distal injection port 414 of the delivery system 50. The recapture sheath 522 and the Touhy-Borst valve 530 are first thoroughly flushed through port 529. Then the distal injection port 414 and the proximal injection port 412 of the deployment handle 400 are preferably flushed through. The distal injection port 414 is in fluid communication with lumen 388 of axially moveable core 304 (as illustrated in FIG. 19A), and proximal injection port 412 is in fluid communication with injection lumens 332 of multilumen shaft 326. The transseptal sheath 520 placement preferably is reconfirmed using fluoroscopy and contrast media injection.

The delivery system 50 as described in the above embodiment, with implant 100 inserted therein, preferably is then inserted into the proximal end of the transseptal sheath 520 (as shown in FIG. 6). To avoid introducing air into the transseptal sheath 520 during insertion of the delivery system 50, a continual, slow flush of sterile heparinized saline preferably is applied through the proximal injection port 412 of the deployment handle 400 to the distal end of the deployment catheter 302 until the tip of the peel-away sheath 314 has been inserted into, and stops in, the hemostatic valve of the transseptal sheath 520. Preferably, the distal tip of the peel-away sheath 314 is inserted approximately 5 mm relative to the proximal end of the transseptal sheath 520.

Under fluoroscopy, the recapture sheath 522 and deployment catheter 302 preferably are advanced, relative to the peel-away sheath 314, approximately 20-30 cm from the proximal end of the transseptal sheath 520, and the system 50 preferably is evaluated for trapped air. The peel-away sheath 314 is preferably not advanced into the transseptal sheath 520 due to a hemostasis valve (not illustrated) on the transseptal sheath 520 blocking its passage. If air is present in the system 50, it may be removed by aspirating through the distal injection port 414, recapture sheath injection port 529, or proximal injection port 412. If air cannot be aspirated, the deployment catheter 302 and recapture sheath 522 preferably are moved proximally and the delivery system 50 preferably is removed from the transseptal sheath 520. All air preferably is aspirated and the flushing/introduction procedure preferably is repeated.

The peel-away sheath 314 preferably is manually slid proximally to the proximal end 524 of the recapture sheath 522. The Touhy-Borst valve 530 preferably is loosened and the deployment catheter 302 preferably is advanced distally relative to the recapture sheath 522 until the deployment handle 400 is within about 2 cm of the Touhy-Borst valve 530 of the recapture sheath 522. This causes the implant 100 to be advanced distally within the transseptal sheath 520 such that the recapture sheath 522 no longer covers the implant 100 or the flexible section 558. The Touhy-Borst valve 530 preferably is tightened to secure the deployment catheter 302 to fix relative movement between the deployment catheter 302 and recapture sheath 522.

Under fluoroscopy, the implant 100 preferably is advanced to the tip of the transseptal sheath 520 by distal movement of the delivery catheter 302. The distal hub 108 of implant 100 preferably is aligned with a transseptal sheath tip radiopaque marker 521 (see FIG. 6). Under fluoroscopy, the sheath 520 positioning within the LAA 10 preferably is confirmed with a distal contrast media injection.

The position of the implant 100 preferably is maintained by holding the deployment handle 400 stable. The transseptal sheath 520 preferably is withdrawn proximally until its tip radiopaque marker 521 is aligned with the distal end of the deployment catheter flexible segment 384. This preferably exposes the implant 100.

Under fluoroscopy, the implant 100 preferably is expanded by rotating the control knob 408 clockwise until it stops. Rotating the control knob 408 preferably releases tension on the control line 312, preferably allowing the implant 100 to expand. The implant 100 preferably is self-expanding. After expansion, any tension on the LAA 10 preferably is removed by carefully retracting the deployment handle 400 under fluoroscopy until the radiopaque marker 360 (see FIG. 19) on the axially movable core 304 moves proximally approximately 1-2 mm in the guide tube 130 (see FIG. 11).

Under fluoroscopy, the expanded diameter (Ø in FIG. 6) of the implant 100 preferably is measured in at least two views to assess the position of the implant within the LAA 10. The measured implant diameter Ø preferably is compared to the maximum expanded diameter.

Preferably, the labeled proximal 412 and distal injection ports 414, of the deployment handle 400 shown in FIG. 19, correlate with the proximal and distal contrast media injections. The proximal contrast media injections are delivered through the delivery catheter lumen 332 to a location proximal to the implant 100. The distal contrast media injections are delivered through the axially movable core 304 to a location distal to the implant 100. Proximal contrast media injections preferably are completed in two views. If the injection rate is insufficient, the recapture sheath injection port 529 may be used independently or in conjunction with the proximal injection port 412 to deliver fluid to a location proximal to the implant 100.

If satisfactory results are seen, any transverse tension on the LAA 10 preferably is released by exposing the flexible segment 384 of the delivery system 50. The flexible catheter section 362 and the flexible core section 372 preferably are linearly co-located to cooperate as the flexible segment 384 of the delivery system 50. This preferably is accomplished by retracting the transseptal sheath 520 proximally approximately 2 cm to expose the flexible segment. By exposing the flexible segment 384, the flexible segment 384 preferably will flex to allow the implant 100 to sit within the LAA 10 free from transverse forces that may be created, for example, by contractions of the heart acting against the transseptal sheath 520 or deployment catheter 302.

Once the flexible segment 384 is exposed, distal contrast media injections preferably are completed in at least two views to verify proper positioning of the implant 100. A flush of saline preferably is used as needed between injections to clear the contrast media from the LAA 10. Following the contrast media injections, the transseptal sheath 520 preferably is advanced distally to cover the flexible segment 384.

If implant 100 position or results are sub-optimal, the implant 100 preferably may be collapsed and repositioned in the LAA 10. To achieve this, under fluoroscopy, the deployment handle 400 preferably is advanced distally to place the radiopaque marker 360 of the axially moveable core 304 at the distal hub 108 of the implant 100. The distal end of the transseptal sheath 520 preferably is aligned with the distal end of the flexible segment 384. The control knob 408 preferably is rotated until the implant 100 has been collapsed to approximately $\frac{1}{3}^{rd}$ or less of its expanded diameter. The control knob 408 preferably acts on the control line 312 to place tension on the proximal hub 104 of the implant 100, pulling the proximal hub 104 of the implant 100 proximally relative the distal hub 108 of the implant 100 to collapse the implant 100. The implant 100 preferably can be repositioned and re-expanded.

The stability of the implant 100 preferably is verified in several views. Stability tests preferably are preformed in the following manner. A contrast media filled syringe preferably is connected to the distal injection port 414 of the deployment handle 400. Under fluoroscopy, at least about a 10 mm gap between the tip of the transseptal sheath 520 and the proximal hub 110 of the implant 100 is preferably confirmed.

The stability of the implant 100 in the LAA 10 preferably is evaluated using fluoroscopy and echocardiography. The recapture sheath Touhy-Borst valve 530 preferably is loosened. Then the deployment handle 400 preferably is alternately retracted and advanced about 5-10 mm while maintaining the position of the transseptal sheath 520 and simultaneously injecting contrast media through the distal injection port 414. This tests how well the implant is held within the LAA 10.

If the implant stability tests are unacceptable, the implant 100 preferably may be collapsed and repositioned as described above. If repositioning the implant 100 does not achieve an acceptable result, the implant 100 preferably may be collapsed and recaptured as described further below.

The implant 100 preferably meets the following acceptance criteria, associated with the assessment techniques listed below, prior to being released. The assessment techniques to be evaluated preferably include 1) residual compression; 2) implant location; 3) anchor engagement; 4) seal quality; and 5) stability. For residual compression, the implant diameter Ø, as measured by fluoroscopic imaging, preferably is less than the maximum expanded diameter of the implant 100. For implant location, the proximal sealing surface of the implant 100 preferably is positioned between the LAA 10 ostium and sources of thrombus formation (pectinates, secondary lobes, etc.) (preferably imaged in at least two views). For anchor engagement, the implant frame 101 preferably is positioned within the LAA 10 so as to completely engage a middle row of anchors 118 in an LAA 10 wall (preferably imaged in at least two views). For seal quality, the contrast injections preferably show leakage rated no worse than mild (preferably defined as a flow of contrast media, well defined, and filling one-third of the LAA 10 during a proximal injection over a period of up to about five ventricular beats, preferably imaged in at least two views). For stability, there preferably is no migration or movement of the implant 100 relative to the LAA 10 wall as a result of the Stability Test.

If implant recapture is necessary, because a different size implant 100 is necessary or desired, or if acceptable positioning or sealing cannot be achieved, the implant 100 preferably is fully collapsed as described above. In one embodiment, once the implant 100 is collapsed, the locking collar 315 of the peel away sheath 314 preferably is unlocked. The peel-away portion 524 of the peel-away sheath 314 preferably is split up to the reinforced section 317 and removed. The reinforced section 317 of the peel-away sheath 314 preferably is slid proximally to the hub of the recapture sheath 522. The Touhy-Borst valve 530 on the proximal end of the recapture sheath 522 preferably is slightly loosened to allow smooth movement of the sheath 522 over deployment catheter 302 without allowing air to enter past the Touhy-Borst valve 530 seal. By removing the peel-away portion 524 of peel-away sheath 314, the recapture sheath 522 can now be advanced further distally relative to the transseptal sheath 520.

While holding the deployment catheter 302 and transseptal sheath 520 in place, the recapture sheath 522 preferably is advanced distally into the transseptal sheath 520 until a half marker band 536 on the recapture sheath 522 is aligned with a full marker band 521 on the transseptal sheath 520. This preferably exposes the recapture flares 510 outside the transseptal sheath.

The collapsed implant 100 preferably is retracted into the recapture sheath 522 by simultaneously pulling the deployment handle 400 and maintaining the position of the recapture sheath 522 until approximately half the implant 100 is seated in the recapture sheath 522. The Touhy-Borst valve 530 on the recapture sheath 522 preferably is tightened over the deployment catheter 302. The recapture sheath 522 and implant 100 preferably are retracted into the transseptal sheath 520 by pulling on the recapture sheath 522 while maintaining the position of the transseptal sheath 520, preferably maintaining left atrial access. The recapture flares 510 of the recapture sheath 522 preferably cover at least some of the anchor elements 195 on the implant 100 as the implant is retracted proximally into the transseptal sheath 520. Further details are described above with respect to FIGS. 13C-13E.

In another embodiment, a collapsed implant 100 may be recaptured using a transseptal sheath 520 with an enlargeable portion 540 as a retrieval catheter 502 system as described above relating to FIG. 15A-15I. Once the implant release and recapture mechanism 200 is properly engaged with the implant 100 and the sock 392 is compressed proximally in order to stow the petals 510 of the recapture section 543 within the transeptal sheath 520, the implant 100 may be presented in a radially-expanded, radially-reduced, or intermediate configuration. Prior to recapture, the implant 100 should be removed from the LAA 10. The enlargeable portion 540 of the retrieval catheter 502 may be in its inflated state to work with the a traumatic tip 542 to reduce incidental trauma to surrounding tissue as the retrieval catheter 502 is advanced distally toward the implant 100. Alternatively, the enlargeable portion 540 may be in its deflated state. The enlargeable portion 540 of the retrieval catheter 502 is deflated in order to allow other components proximal to the retrieval catheter 502 to emerge distally out of the transseptal sheath 520. The retrieval catheter 502 is withdrawn proximally with respect to the implant release and recapture mechanism 200 in order to allow the petals 510 of the recapture section 543 to expand radially. In one embodiment this distance is about 5 cm. Alternatively, a similar effect would result from keeping the retrieval catheter 502 stationary while distally advancing the implant release and recapture mechanism 200 along with the sock attachment section 546 and the implant 100 distally into the heart 5, which would compress the mesh sock 392 and distally advance the recapture section 543 so that the petals 510 would radially expand distal to the end of the recapture catheter 502. The enlargeable portion 540 of the retrieval catheter 502 is inflated to grasp the recapture section 543. Alternatively, the retrieval catheter 502 could be inflated to grasp a distal portion of the sock 392 in order to distally advance the recapture section 543. Advancement of the flexible sock 392 would stretch the sock 392 from a relatively fixed point at the sock attachment section 546, sliding the recapture section 543 distally. The enlargeable portion 540 remains inflated to grasp and move the recapture section 543 to a proximal end 104 of the implant 100 such that the petals 510 substantially surround the collapsed implant 100 and are properly aligned to recapture the implant 100. The enlargeable portion 540 is deflated to allow the implant release and recapture mechanism 200, flares 510, and implant 100 to move proximally with respect to the recapture sheath 502. The implant release and recapture mechanism 200, flares 510, and implant 100 are moved proximally with respect to the recapture sheath 502. As the flares 510 enter the recapture transseptal sheath 502, the flares 510 bend to cover the barbs 118 on the implant 100 which is further radially reduced as it enters the recapture catheter 502. As the implant release and recapture mechanism 200 moves proximally, it moves the sock attachment section 546 with it since both are attached to each other. The implant 100 is recaptured inside the recapture catheter 502. The enlargeable portion 540 may be optionally inflated to lock the implant 100 inside the recapture catheter or to work with the a traumatic tip 542 to shield the body from damage from the end of the catheter 502.

In another embodiment, a collapsed implant 100 may be recaptured using a multi-lumen shaft 326 and a cam 550 system as described above relating to FIGS. 16-18. FIGS. 18A-18H illustrate the recapture of an implant 100 using an implant delivery system 50 with a retrieval catheter system 500 in accordance with one embodiment of the present invention. Once the implant release and recapture mechanism 200 is properly engaged with the implant 100 and the mesh sock 392 is compressed proximally in order to stow the petals or flares 510 of the recapture section 543 within a core lumen 328 of a multi-lumen shaft 326, the implant 100 may be presented in a radially-expanded, radially-reduced, or intermediate configuration. Prior to recapture, the implant 100 should be removed from the LAA 10. The cam 550 is in its non-compressed state with the distal outer surface 558 of the cam 550 in the lumen defined by the first lumen surface 327 of the multi-lumen shaft 326. The multi-lumen shaft 326 is withdrawn proximally with respect to the implant release and recapture mechanism 200 in order to allow the petals 510 of the recapture section 543 to expand radially. In one embodiment this distance is about 5 cm. Alternatively, a similar effect would result from keeping the multi-lumen shaft 326 stationary while distally advancing the implant release and recapture mechanism 200 along with the sock attachment section 546 and the implant 100 distally into the heart 5, which would compress the mesh sock 392 and distally advance the recapture section 543 so that the petals 510 would radially expand distal to the end of the multi-lumen shaft 326. The pull-wires 552 are pulled proximally to actuate the elastic cam 550 into a compressed state to engage a recapture section sheath 544 of a recapture section 543, as described above. Alternatively, the cam 550 could to grasp a distal portion of the sock 392 in order to distally advance the recapture section 543. Advancement of the flexible sock 392 would stretch the sock 392 from a relatively fixed point at the sock attachment section 546, sliding the recapture section 543 distally. The cam 500 remains in its compressed state to grasp and move the recapture section 543 to a proximal end 104 of the implant 100 such that the petals 510 substantially surround the collapsed implant 100 and are properly aligned to recapture the implant 100. The tension in the pull wires 548 is released to allow the cam 550 to revert to its non-compressed state. In some embodiments, the elasticity of the cam 550 will bias the cam 550 to return to its non-compressed state once the tension in the pull wires 548 is released. In some embodiments, the multi-lumen shaft 326 may need to be retracted proximally with respect to the implant release and recapture mechanism 200 in order for the cam 550 to return to its non-compressed state. Once the cam 550 is in its non-compressed state the flares 510 and implant 100 can move proximally with respect to the multi-lumen shaft 326. The implant release and recapture mechanism 200, flares 510, and implant 100 are moved proximally with respect to the multi-lumen shaft 326. As the flares 510 enter the core lumen 328 of the multi-lumen shaft 326, the flares 510 bend to cover the barbs 118 on the implant 100 which is further radially reduced as it enters the core lumen 328 of the multi-lumen shaft 326. As the implant release and recapture mechanism 200 moves proximally, it moves the sock attachment section 546 with it since both are attached to each other. The implant 100 is substantially recaptured inside the multi-lumen shaft 326. The cam 550 may be optionally be actuated into its compressed state in order to lock the implant 100 inside the multi-lumen shaft 326.

If the implant's position and function are acceptable, and implant recapture is not necessary, the implant 100 preferably is released from the delivery system 50. In one embodiment, under fluoroscopy, the transseptal sheath 520 is advanced to the proximal hub 104 of the implant 100 for support. The release knob 410 on the proximal end of the deployment handle 400 preferably is rotated to release the implant 100. Rotating the release knob 410 preferably causes a threaded portion of the distal shaft 344 of the axially movable core 304 to rotate with respect to the threaded aperture 346 such that the threaded portion of the distal shaft 344 preferably is decoupled from the implant 100. Under fluoroscopy, after the axially movable core 304 is decoupled from the implant 100, the release knob 410 preferably is retracted until the distal end 310 of the axially movable core 304 is at least about 2 cm within the transseptal sheath 520.

Under fluoroscopy, while assuring that transseptal access is maintained, the delivery system 50 preferably is retracted and removed through the transseptal sheath 520. Under fluoroscopy, the transseptal sheath 520 position preferably is verified to be approximately 1 cm away from the face of the implant 100. Contrast injections, fluoroscopy and/or echocardiography preferably may be used to confirm proper positioning and delivery of the implant 100 and containment of the LAA 10. The transseptal sheath 520 preferably is withdrawn.

Throughout this application the terms implant and occlusion device have been used. One of ordinary skill in the art will appreciate that all of the disclosures herein are applicable to a wide variety of structures that include both implants that may or may not also be occlusion devices. Routine experimentation will demonstrate those limited circumstances under which certain disclosures and combinations thereof are not beneficial.

Further details regarding left atrial appendages devices and related methods are disclosed in U.S. Pat. No. 6,152,144, titled "Method and Device for Left Atrial Appendage Occlusion," filed Nov. 6, 1998, U.S. patent application Ser. No. 09/435,562, filed Nov. 8, 1999, U.S. patent application Ser. No. 10/033,371, titled "Method and Device for Left Atrial Appendage Occlusion," filed Oct. 19, 2001, and U.S. patent application Ser. No. 10/642,384, filed Aug. 15, 2003, titled "System and Method for Delivering a Left Atrial Appendage Containment Device" published as US 2005-0038470 A1. The entirety of each of these is hereby incorporated by reference.

While particular forms of the invention have been described, it will be apparent that various modifications can be made without departing from the spirit and scope of the invention. Accordingly, it is not intended that the invention be limited, except as by the appended claims.

What is claimed is:

1. A system for retrieving an implantable LAA occlusion device, comprising:
   a delivery catheter having a proximal end and a distal end;
   said delivery catheter adapted for engagement at the distal end of said catheter with an implantable LAA occlusion device of the type having barbs on its exterior surface;
   a recapture section axially movable with respect to said delivery catheter and also extendable from the distal end of the delivery catheter;
   said recapture section including an extendable mesh sock anchored at a first end to a sock attachment section and connected on a second end to a petal carrier connected to a petal;
   said petal carrier adapted for reciprocating motion inside a sheath;
   a sheath having a proximal end and a distal end and a lumen sized to receive the delivery catheter, a portion of the lumen of the sheath being operable from an enlarged inside diameter to a reduced inside diameter to apply an inwardly directed force to the recapture section, such that proximal motion of the sheath enlarges the recapture section;
   said petal carrier adapted to emerge from said sheath when said sheath is in the enlarged state;
   said petal adapted to flare and extend radially and be fixed to said sheath when said sheath is in the reduced diameter state;
   thereby permitting the sheath to advance said petal toward said LAA occlusion device;
   said sock attachment section adapted to apply traction to said petal carrier thereby applying a force to engage said petals with said barbs.

2. The system of claim 1, further comprising an implant releasably engageable with the delivery catheter.

3. The system of claim 2, wherein the implant comprises at least one anchor and is adjustable from an enlarged diameter to a reduced diameter, and wherein the recapture section is configured to cover the at least one anchor when axially extended from the distal end of the delivery catheter.

4. The system of claim 1, wherein the recapture section has reduced configuration and an enlarged configuration capable of receiving at least a portion of the implantable device.

5. The system of claim 1, further comprising an implant actuation shaft, wherein the delivery catheter comprises a lumen extending along the delivery catheter's longitudinal axis, and wherein the implant actuation shaft is disposed at least partially within the lumen.

6. The system of claim 5, further comprising an implant having a distal end in contact with the implant actuation shaft.

7. The system of claim 1, wherein the sheath comprises a balloon.

* * * * *